(12) United States Patent
Johnson et al.

(10) Patent No.: US 9,956,179 B2
(45) Date of Patent: *May 1, 2018

(54) PROCESS AND APPARATUSES FOR PREPARING NANOPARTICLE COMPOSITIONS WITH AMPHIPHILIC COPOLYMERS AND THEIR USE

(75) Inventors: Brian K. Johnson, Princeton, NJ (US); Robert K. Prud'homme, Lawrenceville, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/368,888

(22) Filed: Feb. 8, 2012

(65) Prior Publication Data
US 2012/0171254 A1 Jul. 5, 2012

Related U.S. Application Data

(63) Continuation of application No. 10/472,071, filed as application No. PCT/US02/10715 on Mar. 29, 2002, now Pat. No. 8,137,699.

(60) Provisional application No. 60/280,433, filed on Mar. 30, 2001.

(51) Int. Cl.
| | |
|---|---|
| *A61K 9/14* | (2006.01) |
| *A61K 9/51* | (2006.01) |
| *A01N 25/04* | (2006.01) |
| *A01N 43/70* | (2006.01) |
| *A61K 47/34* | (2017.01) |
| *B01F 7/22* | (2006.01) |
| *B01F 15/00* | (2006.01) |
| *B01J 13/00* | (2006.01) |
| *B01F 1/00* | (2006.01) |

(52) U.S. Cl.
CPC ............ *A61K 9/5138* (2013.01); *A01N 25/04* (2013.01); *A01N 43/70* (2013.01); *A61K 9/5146* (2013.01); *A61K 9/5192* (2013.01); *A61K 47/34* (2013.01); *B01F 7/22* (2013.01); *B01F 15/00123* (2013.01); *B01F 15/00344* (2013.01); *B01F 15/00357* (2013.01); *B01F 15/00376* (2013.01); *B01F 15/00396* (2013.01); *B01J 13/0021* (2013.01); *B01F 1/00* (2013.01)

(58) Field of Classification Search
CPC ..................................................... A01N 25/04
See application file for complete search history.

(56) References Cited

U.S. PATENT DOCUMENTS

| | | | |
|---|---|---|---|
| 5,298,246 A * | 3/1994 | Yano et al. ................ 424/94.1 |
| 5,560,932 A | 10/1996 | Bagchi et al. | |
| 5,578,325 A * | 11/1996 | Domb et al. ................ 424/501 |
| 5,736,152 A * | 4/1998 | Dunn ........................... 424/426 |
| 5,891,907 A | 4/1999 | Kolter et al. | |
| 6,746,635 B2 | 6/2004 | Mathiowitz et al. | |
| 7,687,071 B1 | 3/2010 | Heger et al. | |
| 2004/0166168 A1 | 8/2004 | Mathiowitz et al. | |

FOREIGN PATENT DOCUMENTS

WO    2000/033820    6/2000

OTHER PUBLICATIONS

Ethyl lactate, PUBMED, 2005, 46 pgs.*
Ethyl acetate, PUBMED, 2004, 97 pgs.*
2-butanone, PUBMED, 2005, 129 pgs.*
Welter, B.H., et al. "Simple Mixing Device to Reproducibly Prepare Cationic Lipid-DNA Complexes (Lipoplexes)." BioTechniques. 1999;27(2):286-290.
Wilhelm, M., et al. "Poly(styrene-ethylene oxide) block copolymer micelle formation in water: a fluorescence probe study" Macromolecules. Mar. 1, 1991;24(5):1033-1040.
Bahadur, P., et al. "Interaction Studies of Styrene-Ethylene Oxide Block Copolymers with Ionic Surfactants in Aqueous Solution." Colloids and Surfaces. 1988;29:343-358.
Jones, M., et al. "Polymeric micelles—a new generation of colloidal drug carriers." Eur J Pharm Biopharm. Sep. 1999;48(2):101-11.
Molpeceres, J., et al. "Application of central composite designs to the preparation of polycaprolactone nanoparticles by solvent displacement." J Pharm Sci. Feb. 1996;85(2):206-13.

(Continued)

*Primary Examiner* — Kyle A Purdy
(74) *Attorney, Agent, or Firm* — Robert C. Netter, Jr.; Dann, Dorfman, Herrell & Skillman

(57) ABSTRACT

This invention discloses a process for making nanoparticles of amphiphilic copolymers by flash precipitation. Nanoparticles may be of amphiphilic copolymer alone or may contain an additive target molecule, preferably an organic active. The inclusion of additive target molecules in amphiphilic copolymer nanoparticles can alter their water solubility characteristics, fluid dynamics, and/or stability. Changing an additive target molecule's solubility and stability in a nanoparticle can make a water insoluble compound suitable for pharmaceutical administration as well as specifically target the molecule to a specific area of a patient's body. The process affords the production of nanoparticles at high absolute active content, at high yield, high productivity, and high processing rates while using unusually low amounts of amphiphilic copolymers. Furthermore, the resulting particles exhibit sufficient stability for post processing as desired. The invention also discloses two apparatuses for the production of nanoparticles of amphiphilic copolymers by flash precipitation.

48 Claims, 10 Drawing Sheets

(56) References Cited

OTHER PUBLICATIONS

Alexandridis, P., et al. "Surface Activity of Poly(ethylene oxide)-block-Poly(propylene oxide)-block-Poly(ethylene oxide) Copolymers." Langmuir. 1994;10:2604-2612.
Seo, Y. S., et al. "Effect of interfacial tension on micellization of a polystyrene-poly(ethylene oxide) diblock copolymer in a mixed solvent system." Polymer. 2002;43:5629-5638.
Gindy, M.E., et al. "Composite Block Copolymer Stabilized Nanoparticles: Simultaneous Encapsulation of Organic Actives and Inorganic Nanostructures." Langmuir. 2008;24:83-90.
Johnson, B.K., et al. "Flash NanoPrecipitation of Organic Actives and Block Colpolymers using a Confined Impinging Jets Mixer." Aust. J. Chem. 2003;56:1021-1024.
Liu, Y., et al. "Ostwald Ripening of Beta-Carotene Nanoparticles." Phys Rev Letters. Jan. 19, 2007;98:036102-1-036102-4.

\* cited by examiner

| Example ID | Solvent Velocity m/s | Non-solvent Velocity m/s | Volume% < 1060 nm |
|---|---|---|---|
| PM2-46 | 0.44 | 1.3 | 89 |
| PM2-46C | 0.36 | 1.3 | 89 |
| PM2-47 | 0.24 | 1.3 | 87 |

PROCESS AND APPARATUSES FOR PREPARING NANOPARTICLE COMPOSITIONS WITH AMPHIPHILIC COPOLYMERS AND THEIR USE

RELATED APPLICATIONS

The present application is a continuation application of U.S. patent application Ser. No. 10/472,071, filed on Oct. 23, 2003, now U.S. Pat. No. 8,137,699 which is a § 371 application of PCT/US02/10715, filed Mar. 29, 2002, which claims priority from U.S. provisional application 60/280,433 filed Mar. 30, 2001. The entire disclosure of each of the foregoing applications is incorporated by reference herein.

FIELD OF THE INVENTION

The present invention relates to processes and apparatuses for preparing compositions of small particles from amphiphilic copolymers, often smaller than 100 nm, capable of maintaining sufficient stability for post processing or for transporting or targeting an additive target molecule. These particles are referred to herein as "nanoparticles." When these particles contain an additive target molecule, they are often smaller than 1060 nm in diameter. The process presents a means of controlling the size of the particles and can be used to mix various additives with the nanoparticles for a wide range of uses.

BACKGROUND OF THE INVENTION

Nanoparticles can be used as micro-reactor vessels, to modify the flow properties of materials, or for delivery of pharmaceutical, cosmetic or agricultural agents. In addition, formation of nanoparticles with polymers has been used in various industries to modify the miscible and volatile properties of target molecules. For instance, nanoparticles can be used to create a drug delivery system for therapeutic agents that are hydrophobic in nature and cannot be administered either orally or through intravenous injection because they are not water-soluble. Such therapeutic agents can be incorporated into nanoparticles dispersed in an aqueous solution resulting in a composition that is suitable for injection, inhalation, or oral administration. In addition, the particles can be made small enough for filtration purification and to assure that the nanoparticles will not clog capillaries or alveoli. Also, smaller particles can enhance transfer rates to the body or foliage due to the associated increase in the surface area per volume.

Some polymers have been found to be mucoadherents or have been shown to bind preferentially to mucosal linings in vitro. One such polymer contains polyacrylic acid ("PAA"), which is considered an appropriate vehicle for oral administration because when presented on the surface of a nanoparticle it demonstrates adherence to the gastro-intestinal tract and can improve drug delivery in the lower intestinal tract. PAA also demonstrates a high non-covalent affinity for vaginal mucosal lining. Mucoadhesive properties in a drug coating can be used to target a highly potent or water insoluble drugs to a targeted area in the patient. By targeting the drug to a mucosal lining, a lower dose may be administered with the same therapeutic effect. In addition, an altered water solubility of a drug should increase its bioavailability.

Additional polymers that are mucoadherents and are potential components in pharmaceutical formulations include poly(d-glucosamine), poly(d-glucaronic acid-N-acetylglucosamine), poly(N-isopropylacrylamide), poly(vinyl amine), and poly(methacrylic acid). "Mucoadhesion of polystyrene nanoparticles having surface hydrophilic polymeric chains in the gastrointestinal tract" *International Journal of Pharmaceutics* 177 (1999) 161-172. "Bioadhesion Technologies for the delivery of Peptide and Protein Drugs to the Gastrointestinal Tract" *Critical Reviews in Therapeutic Drug Carrier Systems* 11(2&3):119-160 (1994). "pH-Dependant Dissolving Nano- and Microparticles for improved Peroral Delivery of a Highly Lipophilic Compound in Dogs" *AAPS PharmSci* 2001; 3 (1) article 8.

Polyethylene oxide ("PEO") is another desirable compound for use in pharmaceutical compositions. For example, liposomes with PEO on the exterior surface have been shown useful to prolong blood circulation lifetimes, decrease the rate of uptake into the mononuclear phagocyte system, and allow crossing in vivo biological bathers. PEO liposomes also have been shown to decrease the toxicity and increase the stability of an administered drug. "Interaction of PEG-Phospholipid Conjugates with phospholipid Implication in the Liposomal Drug Delivery," *Advanced Drug Delivery Reviews*, 16:235-247 (1995). "Long Circulating (sterically stabilized) Liposomes for targeted drug delivery," TiPS 15:215-220 (1994).

The formation of nanoparticles has been achieved by various methods. Nanoparticles can be made by precipitating a molecule in a water-miscible solvent, and then drying and pulverizing the precipitate to form nanoparticles. (U.S. Pat. No. 4,726,955). Similar techniques for preparing nanoparticles for pharmaceutical preparations include wet grinding or milling. Other methods include mixing low concentrations of polymers dissolved in a water-miscible solution with an aqueous phase to alter the local charge of the solvent and form a precipitate through conventional mixing techniques. (U.S. Pat. No. 5,766,635). Other methods include the mixing of copolymers in organic solution with an aqueous phase containing a colloid protective agent or a surfactant for reducing surface tension. Other methods of incorporating additive therapeutic agents into nanoparticles for drug delivery require that nanoparticles be treated with a liposome or surfactant before drug administration (U.S. Pat. No. 6,117,454).

Typically, current methods for forming nanoparticles by precipitation demonstrate little or no control of particle size and show poor yields. Uncontrolled and unpredictable particle size is particularly disadvantageous in the formation of pharmaceutical and agricultural products. Furthermore, large scale production of nanoparticles using established methods can be quite costly due to the low concentration of polymer initially introduced into the process solvent prior to nanoparticle production. Finally, many production techniques such as milling or wet grinding introduce the possibility of contamination into the final product.

In addition, methods for forming nanoparticles with additive target molecules contained within the nanoparticle typically have been performed with additives at very low ratios compared with copolymer and at low absolute concentration. Therefore, the fraction of additive target molecule per nanoparticle is minimal, and the cost of production is high. Lowering the ratio of copolymer to additive target molecule is desirable to increase the number of resulting nanoparticles that contain additive target molecule and the amount of additive target molecules contained within the nanoparticles as well as reduce the amount of initial copolymer needed to create these nanoparticles.

For the foregoing reasons, there is a need for a process of creating nanoparticles with copolymers in which the size of the resulting nanoparticle can be predicted and controlled, additives can be incorporated into the nanoparticle at a high yield, and the amount of copolymer initially needed is reduced. Furthermore, there is a long felt need for a process of producing nanoparticles at a high concentration and in which the nanoparticles produced can be harvested easily and with a high yield.

SUMMARY OF THE INVENTION

The present invention is directed to a process and apparatuses for carrying out that process in which nanoparticles are created from amphiphilic copolymers at a predictable and controlled size and yield. The formation of nanoparticles is induced by mixing at least one process solvent comprising amphiphilic copolymers with at least one non-process solvent capable of changing the charge of the local molecular environment of the amphiphilic copolymers. Optionally, the process solvent(s) or non-process solvent(s) can contain an additive target molecule useful for a specific indication which can be coprecipitated or coated with the amphiphilic copolymer. The process solvent or non-process solvent can also contain supplemental additives useful for the production or subsequent use of the nanoparticles.

The apparatuses for carrying out the processes disclosed herein use a controlled mixing velocity in either a batch or continuous configuration for introduction of the process solvent and non-process solvent streams. The introduction of the process streams into these mixers allows a "flash" precipitation to occur yielding nanoparticles. The nanoparticles produced exhibit sufficient stability for post processing for use in pharmaceutical, medical, or agricultural applications.

The process of mixing molecules of initially separate fluids to homogeneity is called "micromixing." The time to achieve homogeneity is identified by the characteristic micromixing time $\tau_m$, or simply the mixing time. Copolymer precipitation occurs in a finite time, which is identified as $\tau_{agg}$ and the characteristic time for target molecule, an organic active, precipitation is designated as $\tau_{ng}$. The mixing time is controlled by the physical operation of the mixer and the precipitation times are controlled by the initial choices of compositions and conditions for mixing and the compositions existing and conditions at the molecular level during the mixing process.

The ratio of each of these times can effect the size and yield of the micro- or nanoparticles produced. Marcant and David have shown the rate at which the two fluids are micromixed can control the resulting particles sizes in precipitation. Marcant and David. Experimental-Evidence for and Prediction of Micromixing Effects in Precipitation. *AIChE Journal* 37(11): 1698-1710 (1991). In the case of nanoparticles, the same principles can apply, but due to the very small size of nanoparticles, the process occurs very fast, essentially in a "flash." A mixer that is sufficiently fast to reduce the mixing time, $\tau_m$, of the fluids to below the precipitation times, $\tau_{agg}$ and $\tau_{ng}$, can critically effect the process.

In the present invention, micromixing is achieved by using either a continuous flash mixer or a batch flash mixer. The flow rate, temperature, and pressure of each stream entering or in the mixer can be controlled. Additionally, a centripetal mixer can be used for flash precipitation of nanoparticles from amphiphilic copolymers.

In a continuous flash mixer at least one process solvent and at least one non-process solvent are continually added to a mixing vessel through inlet tubes. The resulting mixture is removed from the mixer for a period of time under a steady state condition. In one embodiment, the process solvent(s) and a non-process solvent(s) are introduced into a mixing vessel through separate inlet tubes. The tubes are introduced in a confined region where intimate mixing of the stream can occur rapidly and locally mix in the ratio they were charged. The confined region is enclosed and beneficial to enhancing the mixing. In another embodiment the confined region is open and the streams are directed substantially towards one another to facilitate rapid or controlled mixing or are in the presence of a mechanical agitator to facilitate rapid or controlled mixing.

In a batch flash mixer, the non-process solvent is placed in a mixing vessel. The process solvent(s) and any additional non-process solvent(s) are introduced into a mixing vessel containing the non-process solvent through at least one inlet tube at a controlled flow rate and temperature. In a batch flash mixer, the process is not at steady state and the contents of the mixer are continually changing as solvent stream(s) is added to the batch. The batch is completed after the solvent streams have been added. In one embodiment, the added solvent stream(s) is introduced in a region near a mechanical agitator, where the mixing velocity is the greatest or is most easily controlled. This point of introduction could also be a confined portion of the mixing vessel, such as in a recycle loop. An agitator is not required if the fluids added into the non-solvent have a high mixing velocity sufficient to mix the fluid contents rapidly and in a controlled fashion.

Nanoparticles can be formed by dissolving an amphiphilic copolymer in a process solvent at a concentration of at least 0.1% by weight, but preferably the concentration of copolymer is at least 0.2% by weight. Examples of amphiphilic copolymers include but are not limited to block copolymers, graft copolymers, and random copolymers that include both hydrophobic and hydrophilic regions within the same copolymer. The process solvent includes, but is not limited to, alcohols and ethers. The process solvent can be heated or pressurized or both to facilitate dissolution of the amphiphilic copolymer, depending on the dissolution characteristics of the copolymer in the solvent. Upon micromixing the process solvent containing the amphiphilic copolymer with a non-process solvent, the amphiphilic character of the copolymer becomes apparent and either the hydrophobic portion or the hydrophilic portion of the copolymer can no longer exist in the soluble state, and thus precipitates. The soluble portion of the amphiphilic copolymer affords steric or steric and electrostatic stabilization of the nanoparticles sufficient for post processing or harvesting.

In one embodiment of the present invention, additive target molecules can be added to the amphiphilic copolymer in the process solvent. Upon creation of nanoparticles with the amphiphilic copolymer, the additive target molecules will be incorporated in the nanoparticle. Additive target molecules that are poorly soluble in the non-process solvent are coprecipitated, coated, encapsulated, or confined as a particulate core and stabilized by the amphiphilic copolymer. The nanoparticles maintain a small and stable size for a time sufficient for post processing. The additive target molecules can be organic actives useful for a pharmaceutical indication and poorly soluble in aqueous systems. Amphiphilic copolymers and the additive target molecules can be mixed in a ratio between about 1:20 to about 20:1 by weight and result in nanoparticles of amphiphilic copolymers with additive target molecule.

In another embodiment of the invention, supplemental additives such as colloidal dispersants or surfactants can be included in the final colloid mixture to enhance the resultant properties of the nanoparticles, such as stabilization the nanoparticles.

The flash precipitation process and the associated flash mixing apparatuses described herein are useful for the production of amphiphilic copolymer nanoparticle compositions including optional additive target molecules. With the process and apparatuses described herein, nanoparticles compositions can be made with a high content of target molecule with high yield, high productivity, and high processing rates while using low amounts of amphiphilic copolymers. The nanoparticles compositions and process described can be used for a variety of purposes including creating pharmaceutical, medical, and agricultural formulations and particle surface functionalization.

These and other features, aspects, and advantages of the present invention will become better understood with reference to the following descriptions and appended claims.

BRIEF DESCRIPTION OF THE DRAWINGS

The following Figures are included in this application to exemplify and describe the invention but are not intended to limit the embodiments of the invention.

DETAILED DESCRIPTION OF THE INVENTION

The present invention relates to a process and apparatuses preparing nanoparticles from amphiphilic copolymers. The size of the resulting nanoparticles can be controlled by controlling the mixing velocity used to create them. Nanoparticles can be produced from amphiphilic copolymers that are dissolved in a process solvent. After the amphiphilic copolymers are dissolved in the process solvent, the solution is rapidly mixed with a non-process solvent and nanoparticles are flash precipitated in the resulting solution. This mixing can be achieved through various methods during which the mixing velocity is controlled. In addition, an additive target molecule can be mixed with the amphiphilic copolymer in the process solvent prior to flash precipitation for incorporation into the resulting nanoparticles.

In the present invention, mixing apparatuses are presented that are capable of reaching a critical and robust processing condition or a very fast mixing velocity and capable of controlling the size of the nanoparticles, by controlling mixing time ("$\tau_m$") through control of the mixing velocity. The types of mixing apparatuses presented include a continuous flash mixer and a batch flash mixer. Mixing velocity is critical to controlling the nanoparticle size distribution, however, quantifying the actual $\tau_m$ is difficult. Therefore, it is practical to use the mixing velocity as an indicator of mixing time. For the examples presented below that were performed using a continuous flash mixer, the mixing velocity was considered to be the highest average velocity of any of the fluids entering the mixing vessel. For the examples presented that were performed in a batch flash mixer, mixing velocity was considered to be the greater of either the moving surface velocity created by the tip speed or the average velocity of the incoming fluid. Actual mixing velocities may have been higher or lower than the estimated mixing velocity of a single solvent stream or mix speed due to the cumulative effect of two fluids or moving surfaces coming together.

A process solvent is a composition comprised of one or more fluid components and capable of carrying a solid or solids in solution or suspension. The process solvent is able to substantially dissolve the amphiphilic copolymer to a molecularly soluble state. A non-process solvent is any composition that is substantially soluble with the process solvent and leads to the precipitation of the dissolved or suspended amphiphilic copolymer after mixing with the process solvent. Precipitation of the amphiphilic copolymer upon mixing can be the result of changes in temperature, composition, or pressure or any combination of each. The process stream and non-process stream refer to the process and non-process solvents with the optional additive target molecules or supplemental additives, respectively as they enter the mixer.

Flash Mixers

Figure 1:
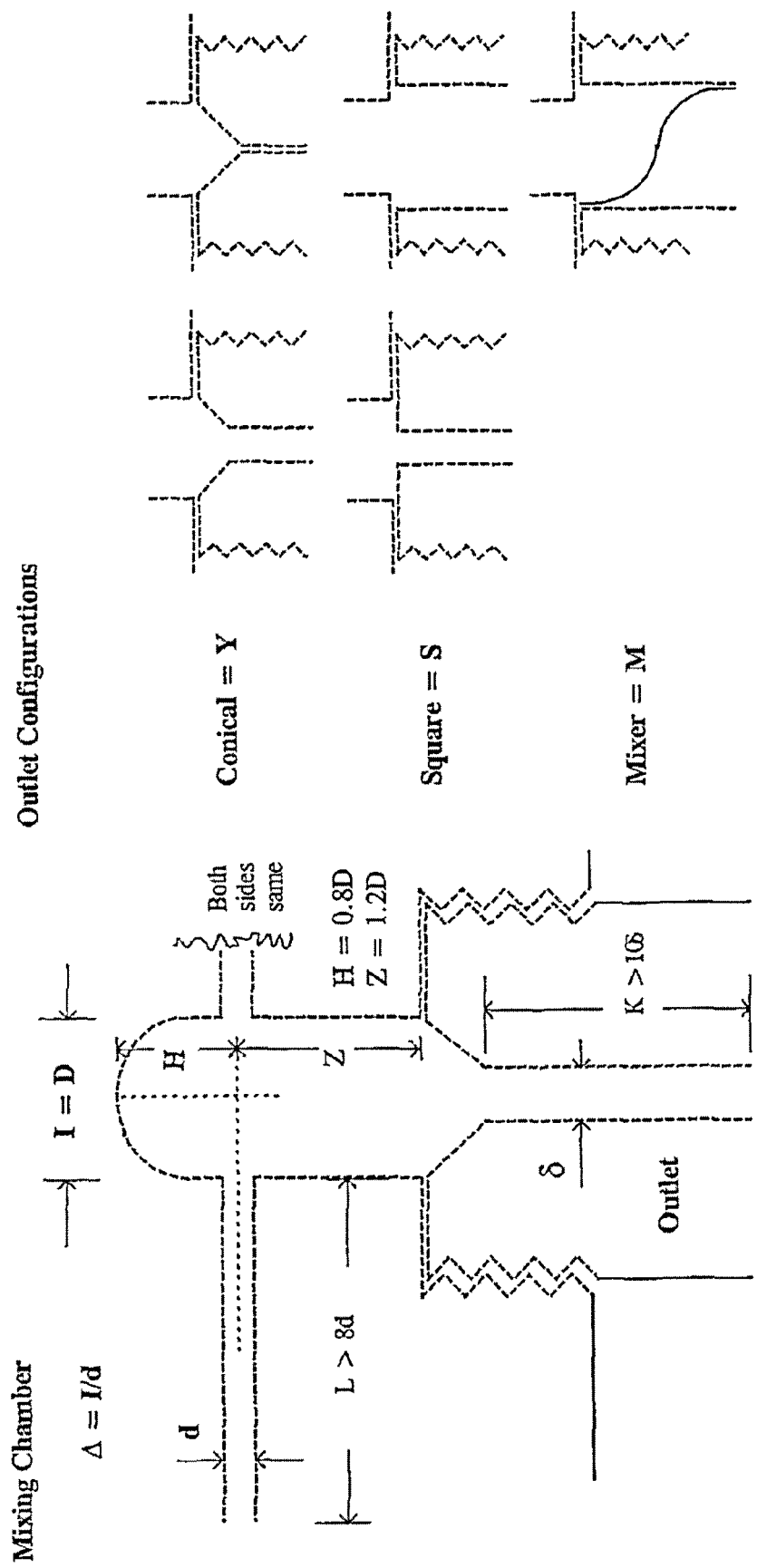
FIG. 1 is a schematic drawing of a continuous flash mixer, presenting two inlets to a conical-domed mixing vessel with a conical outlet, a variety of outlet shapes are also presented including a conical, square and mixed shape outlets at two different opening sizes.

An example of a continuous flash mixer is shown in FIG. 1. Two solvent streams of fluid are introduced into a mixing vessel through independent inlet tubes having a diameter, d, which can be between about 0.25 mm to about 6 mm but are between about 0.5 mm to about 1.5 mm in diameter for laboratory scale production. The continuous flash mixer includes temperature controlling elements for fluid in the inlet tubes and in the mixing vessel. In one embodiment, the inlet tubes are coiled in a water bath that controls the temperature of the fluids passing through the tubes and the mixing vessel is placed in a water bath. In addition, the mixing vessel contains a device to control and regulate the pressure of its contents. In one embodiment of the invention, the solvent streams are impacted upon each other while being fed at a constant rate from the inlet tube into the mixing vessel. In another embodiment of the invention, more than two inlet tubes direct solvent streams into the mixing vessel.

In one embodiment, the mixing vessel is a cylindrical chamber with a hemispherical top. The diameter of the mixing vessel, D, is typically between 1.25 mm to about 30.0 mm but preferably is between about 2.4 mm to about 4.8 mm, and D/d is about 3 to 20. The mixing vessel also contains an outlet with a diameter, $\delta$, that can be between about 0.5 mm to about 2.5 mm but is preferably between 1.0 mm to about 2.0 nm, and $\delta$/d is about 1 to 5. In one embodiment, the outlet can be conical, in another embodiment it can be square, and in another it can have a mixed configuration.

For the continuous flash mixer shown in FIG. 1, the mixing velocity is considered the highest average velocity of any of the fluid streams entering the mixing vessel. If the interior of the mixing vessel is made large, D/d>40, the inlet tubes delivering the fluids to be mixed can protrude into the interior of the vessel to direct fluid impact within the vessel and to ensure rapid mixing.

The mixing velocity is considered the highest average velocity of any of the fluid streams entering the mixing chamber. In one embodiment of the invention, the angle of incidence of the two streams can be varied. The angling of the inlet streams can affect the mixing velocity. For example, in one embodiment of the invention, the streams are directed towards each other causing them to collide and essentially increasing the mixing velocity while decreasing the mixing time. In one embodiment, the velocity of the fluid exiting the inlet tube is between about 0.02 m/s and 12.0 m/s.

In one embodiment, the mixing vessel is a continuous centripetal mixer. In this embodiment, the process and non-process streams are directed into a mixing vessel but do not directly impinge. The streams are forced to the walls of the mixing vessel by centripetal forces. In another embodiment, the mixing vessel could be another high mixing velocity or highly confined mixer such as, but not limited to, a static mixer, rotor stator mixer, or a centripetal pump where the process solvent is introduced into the region of high mixing velocity. To those skilled in the art, any mixer capable of providing a sufficient mixing velocity with controlled introduction of the process streams could afford a flash precipitation under the teachings of this disclosure.

In another embodiment of the invention, the dimensions of the continuous flash mixer can be scaled up to achieve desired production rates. In this embodiment, the process is performed at a steady state with the streams continually introducing the desired composition ratio and continually draining from the mixing vessel. The effluent can be collected in a second holding tank, optionally with a liquid phase within, for further post processing.

Figure 2:
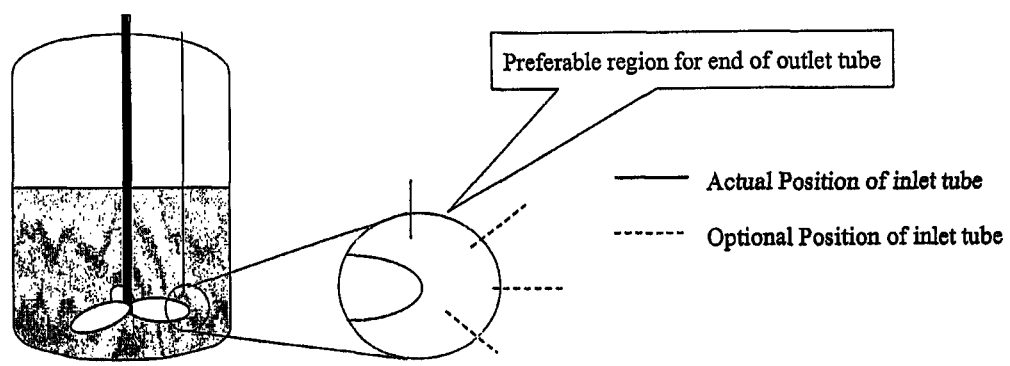
FIG. 2 is a schematic drawing of a batch flash mixer in which the mixing mechanism is shown with a preferable position for the end of the inlet tube in relation to the mixing or agitating device.

In another embodiment of the invention, the process and non-process solvents are mixed in a batch flash mixer. An example of a batch flash mixer is presented in FIG. 2. In this design, the process solvent stream containing the amphiphilic copolymer and the optional additive target molecule are added via an inlet tube to a non-process solvent in a mixing vessel that has a mechanical agitator. The batch flash mixer includes temperature controlling elements for fluids in the inlet tubes and mixing vessel. In one embodiment, the inlet tube is coiled in a water bath that controls the temperature of the fluid passing through the tube and the mixing vessel is submerged in a water bath. In addition, the mixing vessel contains a device to control and regulate the pressure of its contents.

Fluid is introduced via an inlet tube into the region of high mixing intensity, near the sweep region of the mechanical agitator. In a preferred embodiment, a marine agitator with a single baffle is used in the batch flash mixer, but other agitators or baffle configurations could be employed. The placement of the incoming solvent stream can be varied by varying the position of the inlet tube, but the fluid exiting the inlet tube is usually fed directly into the region of high mixing intensity. The distance between the end of the inlet tube and the agitator tip is preferably within 15% of the agitator diameter of the circular sweep made by the agitator. This ratio facilitates rapid incorporation of the incoming fluid into the swept region of the mechanical agitator or rapid mixing with the immediate outflow of the mechanical agitator. In one embodiment, the velocity of the fluid exiting the inlet tube is between about 0.02 m/s and 12.0 m/s. In another embodiment, the surface velocity of the fluid in the mixing vessel is between about 0.02 m/s and 8.5 m/s.

In one embodiment of the invention, the batch flash mixer includes multiple inlet tubes for the introduction of more than one solvent stream. In one embodiment of the invention, amphiphilic copolymer and additive target molecule are introduced into the mixing vessel via different solvent streams. In another embodiment, the fluid streams can be directed towards each other to substantially cause them to collide and mix. In another embodiment of the invention, the dimensions of the batch flash mixer can be scaled up to achieve desired production rates with limited scale up of the inlet tube diameter relative to the agitator.

For the examples provided below in which a continuous flash mixer was used, a constant flow rate was provided by a syringe pump for each inlet tube using a Harvard Apparatus (model number 7023). At least one 100 mL glass syringe (SGE Inc.) was connected to each side of the mixer in FIG. 1. For each side of the mixers, the fluid to be mixed flowed from the syringe pumps into a coil of $\frac{1}{8}^{th}$-inch stainless steel through a narrowing tube and into the mixing vessel. The $\frac{1}{8}^{th}$-inch coil and the continuous flash mixer were submerged in a temperature bath to control the temperature of the fluid entering the continuous flash mixer. The outlet of the mixer was connected to an 8-inch line of $\frac{1}{8}^{th}$-inch tubing leading out of the temperature bath for product collection.

For the examples provided below in which a continuous flash mixer was used, a constant flow rate was provided by a syringe pump for each inlet tube using a Harvard Apparatus (model number 7023). At least one 100 mL glass syringe (SGE Inc.) was connected to each side of the mixer in FIG. 1. For each side of the mixer, the fluid to be mixed flowed from the syringe pumps into a coil of $\frac{1}{8}^{th}$-inch stainless steel through a narrowing tube and into the mixing vessel. The $\frac{1}{8}^{th}$-inch coil and the continuous flash mixer were submerged in a temperature bath to control the temperature of the fluid entering the continuous flash mixer. The outlet of the mixer was connected to an 8-inch line of $\frac{1}{8}^{th}$-inch tubing leading out of the temperature bath for product collection.

For the examples presenting a batch flash mixer, the process solvent was injected through an inlet tube at a constant flow rate by a syringe pump (model number 7023, Harvard Apparatus) comprising at least one 100 mL glass syringe (SGE, Inc.) into the mixing vessel containing the non-process solvent. The stream flowed from the syringe pump and into a coil of $\frac{1}{8}^{th}$-inch stainless steel through a narrowing device into a 1.0 mm-tube and into the mixing vessel. The $\frac{1}{8}^{th}$-inch coil was submerged in a temperature bath to control the temperature of the fluid entering the batch flash mixer. The temperature of the contents of the batch flash mixer can be varied using conventional means including hot plates and water baths.

In the case of the centripetal mixer, the non-solvent was supplied using a pressurized vessel and the flow rate was controlled by adjusting the pressure of the vessel or using a control valve. A Harvard Apparatus with a 100 mL syringe was also used with this mixer.

Amphiphilic Copolymers

Amphiphilic copolymers are comprised of sub-units or monomers that have different hydrophilic and hydrophobic characteristics. Typically, these sub-units are present in groups of at least two, comprising a block of a given character, such as a hydrophobic or hydrophilic block. Depending on the method of synthesis, these blocks could be of all the same monomer or contain different monomer units dispersed throughout the block, but still yielding blocks of the copolymer with substantially hydrophilic and hydrophobic portions. These blocks can be arranged into a series of two blocks (diblock) or three blocks (triblock), or more, forming the backbone of a block copolymer. In addition, the polymer chain can have chemical moieties covalently attached or grafted to the backbone. Such polymers are graft polymers. Block units making up the copolymer can occur in regular intervals or they can occur randomly making a random copolymer. In addition, grafted side chains can occur at regular intervals along the polymer backbone or randomly making a randomly grafted copolymer. The amphiphilic copolymers used in this invention are comprised of blocks of at least two sub-units or with a minimum contour length the equivalent of at least 5 ethylene units and of a given character and a molecular weight of at least 300 g/mole. Contour lengths are the linear sum of the polymer backbone, the molecular dimensions of which can be approximated using the *Polymer Handbook*, 4$^{th}$ Edition, eds. J. Brandrup, E. H. Immergut, and E. A. Grulke, assoc. ed. A. Abe, D. R. Bloch, 1999, New York, John Wiley & Sons, the disclosure of which is hereby incorporated by reference in its entirety.

Amphiphilic copolymers could also contain a polymeric block or blocks as given herein connected to a moiety of considerable size that is not a polymeric chain consisting of sub units. In this case the molecular weight of the moiety is greater than 300 g/mole. It is often preferable to have the moiety be at least 1000 g/mole to enhance the post mixing soluble or non-soluble character of the moiety.

Amphiphilic copolymers possess both hydrophobic and hydrophilic regions along the same polymer chain. Hydrophobic and hydrophilic regions maybe comprised of blocks of polymer or may have their hydrophilicity/hydrophobicity affected by a grafted moiety. The unique characteristics of an amphiphilic copolymer allows the copolymer to precipitate locally when its solvent conditions are changed. For instance, an amphiphilic copolymer dissolved in a charge-neutral solvent should locally precipitate when mixed with charged solvent causing the hydrophilic regions to take a conformation maximizing contact with the charged solvent and the hydrophobic regions to minimize contact with it or locally precipitate. Preferably, the hydrophilic block should be at least 1000 g/mole to facilitate colloidal stability via steric or steric and electrostatic means after nanoparticle formation. Preferably, the hydrophobic block is of at least 1000 g/mole to enhance the non soluble character of the block and promote precipitation.

Nanoparticles formed by the process of this invention can be formed with graft, block or random amphiphilic copolymers. These copolymers can have a relatively low molecular weight, between 1000 g/mole and 50,000 g/mole, or preferably between about 3000 g/mole to about 25,000 g/mole, and more preferably at least 2000 g/mole. Alternatively, the amphiphilic copolymers used in this invention exhibit a surface tension when dissolved in water at 0.1 wt % of at least 50 dynes/cm.

Examples of suitable hydrophobic sub-units that comprise hydrophobic blocks in an amphiphilic copolymer include but are not limited to the following: acrylates including methyl acrylate, ethyl acrylate, propyl acrylate, n-butyl acrylate ("BA"), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and vinylimidazole; aminoalkyls including aminoalkylacrylates, aminoalkylsmethacrylates, and aminoalkyl(meth)acrylamides; styrenes; and lactic acids. Examples of suitable hydrophilic sub-units in an amphiphilic copolymer include but are not limited to the following: carboxylic acids including acrylic acid, methacrylic acid, itaconic acid, and maleic acid; polyoxyethylenes or polyethyleneoxide; and unsaturated ethylenic mono or dicarboxylic acids. Preferably the blocks are either diblock or triblock in nature. Preferably, block copolymers for this invention include blocks substantially comprising the monomers of polystyrene, polyethylene, polybutyl acrylate, polybutyl methacrylate, polylactic acid, polyacrylic acid, polyoxyethylene or those that are biocompatible. Additional preferable polymers shown to be mucoadherents and preferable for incorporation into amphiphilic copolymers include, but are not limed to, monomers of poly(acrylic acid), poly(d-glucosamine), poly(d-glucaronic acid-N-acetylglucosamine), poly(N-isopropylacrylamide), poly(vinyl amine), and poly(methacrylic acid).

In graft copolymers, the length of a grafted moiety can vary. Preferably, the grafted segments are alkyl chains of 4 to 18 carbons or equivalent to 2 to 9 ethylene units in length. In addition, the grafting of the polymer backbone can be useful to enhance solvation or nanoparticle stabilization properties. A grafted butyl group on the hydrophobic backbone of a diblock copolymer of a polyethylene and polyethylene glycol should increases the solubility of the polyethylene block. Suitable chemical moieties grafted to the block unit of the copolymer comprise alkyl chains containing species such as, but not limited, to amides, imides, phenyl, carboxy, aldehyde or alcohol groups.

The amphiphilic copolymer can be selected from several groups of copolymers including polystyrenes, polyethyleneglycols, polyglutamic acids, hyaluronic acids, polyvinylpyrrolidones, polylysines, polyarginines, alginic acids, polylactides, polyethyleneimines, polyionenes, polyacrylic acids, and polyiminocarboxylates. Any biocompatable amphiphilic copolymer can be used. Preferably, the amphiphilic copolymer is comprised of diblock or triblock compositions containing at least one of the following: a polystyrene block, a polyethylene oxide block, a polybutylacrylate, a polyacrylic acid, polybutylmethacrylate block, or a polyethyleneoxide block.

Additive Target Molecules

The amphiphilic copolymer is dissolved in a process solvent capable of dissolving at least 0.1% of the copolymer by weight and that is typically a liquid at room temperature. In one embodiment of the invention, the process solvent is a mixture of solvents or an organic solvent. In a more preferred embodiment of the invention, the process solvent is an alcohol or ether. In another embodiment, the process solvent is methanol. In yet another embodiment, the process solvent is tetrahydrofuran ("THF"). The concentration of the amphiphilic copolymer in the process solvent may be increased by controlling the temperature and the pressure of the mixture. In the present case, nanoparticle compositions in which amphiphilic copolymers contain PEO as the water soluble component are used for steric stabilization of a target molecule are desirable to obtain the properties for a pharmaceutical formulation. If linked to a hydrophobic species or polymer chain, the amphiphilic copolymer can be used to coat hydrophobic target molecules where the exterior of the particles presents PEO as soluble in an aqueous phase.

In another embodiment of the invention, the process or non-process solvent may consist of a liquefied gas. In this embodiment, the process or non-process solvents are a gas at room temperature but are put in liquid form for the process by changing the pressure or temperature or both in the mixing vessel or inlet tubes. An example of a liquefied gas used as a non-process solvent is carbon dioxide under adequate pressure with or without a modifier, such as ethanol. After mixing, a post processing step consisting of a pressure or temperature change or a change in both is made and the solvent evaporates leaving the nanoparticles.

In another embodiment of the invention, nanoparticles are made and include an additive target molecule. In one embodiment, an additive target molecule is mixed with the amphiphilic copolymer in the process solvent phase. In another embodiment the additive is combined with the amphiphilic copolymer in a ratio of 1:4 to 10:1 by weight or charge. In still another embodiment, the additive target molecule is mixed with the amphiphilic copolymer in at least a 1:2 ratio by weight. Preferably the target molecules is present in the process solvent streams after mixing at a concentration of at least 0.1% by weight, but more preferably the concentration of target molecule is at least 0.2% by weight. The temperature and the pressure of the process solvent can be altered to allow complete dissolution of both the amphiphilic copolymer and the additive target molecule while maintaining a liquid phase. One such solvent would be ethanol and the mixing process is performed at elevated pressure.

Examples of some preferred additive target molecules that may be added to nanoparticles by this process can be selected from the known classes of drugs including immunosuppressive agents such as cyclosporins (cyclosporin A), immunoactive agents, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, anti-oxidants, preservatives, vitamins, and nutrients. Preferred drug substances include those intended for oral administration and intravenous administration. They can be selected from any pharmaceutical organic active and precursor compound. A description of these classes of drugs and a listing of species within each class can be found in *Physicians Desk Reference,* 51 edition, 2001, Medical Economics Co., Montvale, N.J., the disclosure of which is hereby incorporated by reference in its entirety. The drug substances are commercially available and/or can be prepared by techniques known in the art. Other additive target molecules include agricultural compounds, biocides, pesticides, herbicides, fungicides, and insecticides.

In a preferred embodiment, the additive target molecule is an organic active compound that is co-precipitated with the amphiphilic copolymer. The target molecule should be substantially insoluble in solution created after the mixing process is complete. The target molecule is typically supersaturated or above its solubility during the mixing process and precipitates in a characteristic time $\tau_{ng}$. In a more preferable embodiment, the target molecule is poorly soluble in water, 1 wt %, and more preferably <0.1 wt %, at a specific pH. In this case, the target molecule is molecularly soluble in one of the process streams prior to the flash precipitation.

In one embodiment, the target molecule is an anti-oxidant or a provitamin of poor water solubility, <0.1 wt %. For instance, the target molecule could be β-carotene. The amphiphilic copolymer contains a highly hydrophobic block and a hydrophilic block. The hydrophilic block might include a polystyrene-block-polyethyleneoxide ("PEO") block. The process solvent is tetrahydrofuran ("THF") and the non-process solvent is water. In this case, PEO is presented to the outside of the molecule making the material dispersable in water.

Process and Non-Process Solvents

The solution of process solvent containing either amphiphilic copolymer alone or with an additive target molecule is mixed with a non-process solvent. The non-process solvent must be capable of changing the local molecular environment of the copolymer and cause local precipitation of either the hydrophobic or hydrophilic blocks. The non-process solvent can be water that is either distilled, filtered or purified by reverse osmosis (RO") or an aqueous solution containing a buffering agent, salt, colloid dispersant, or inert molecule. The non-process solvent could also be a mixture of solvents, such as alcohol and water. Using flash precipitation process described herein, nanoparticles are formed in the final mixed solution. The final solvent containing the nanoparticles can be altered by a number of post treatment processes, such as but not limited to dialysis, distillation, wiped film evaporation, centrifugation, lyophilization, filtration, sterile filtration, extraction, supercritical fluid extraction, or spray drying. The processes typically occur after the nanoparticle formation but could also occur during the nanoparticle formation process.

Supplemental Additives

One or more supplemental additives can be added to the process solvent or non-process solvent streams or to a stream of nanoparticles after formation by flash precipitation to taylor the resultant properties of the nanoparticles or for use in a particular indication. Examples of supplemental additives include inert diluents, solubilizing agents, emulsifiers, suspending agents, adjuvants, wetting agents, sweetening, flavoring, and perfuming agents, isotonic agents, colloidal dispersants and surfactants such as but not limited to a charged phospholipid such as dimyristoyl phophatidyl glycerol; alginic acid, alignates, acacia, gum acacia, 1,3 butyleneglycol, benzalkonium chloride, collodial silicon dioxide, cetostearyl alcohol, cetomacrogol emulsifying wax, casein, calcium stearate, cetyl pyridinium chloride, cetyl alcohol, cholesterol, calcium carbonate, Crodestas F-110®, which is a mixture of sucrose stearate and sucrose distearate (of Croda Inc.), clays, kaolin and bentonite, derivatives of cellulose and their salts such as hydroxypropyl methylcellulose (HMPC), carboxymethylcellose sodium, carboxymethyl cellulose and its salts, hydroxypropyl celluloses, methylcellulose, hydroxyethylcellulose, hydroxypropylcellulose, hydroxypropylmethylcellulose phthalate, noncrystalline cellulose; dicalcium phosphate, dodecyl trimethyl ammonium bromide, dextran, dialkylesters of sodium sulfosuccinic (e.g. Aerosol OT® of American Cyanamid), gelatin, glycerol, glycerol monostearate, glucose, p-isononylphenoxypolt-(glycidol), also known as Olin 10-G® or surfactant 10-G® (of Olin Chemicals, Stamford, Conn.); glucamides such as octanoyl-N-methylglucamide, decanoyl-N-methylglucamide; heptanoyl-N-methylglucamide, lactose, lecithin (phosphatides), maltosides such as n-dodecyl β-D-maltoside; mannitol, magnesium stearate, magnesium aluminum silicate, oils such as cotton seed oil, corn germ oil, olive oil, castor oil, and sesame oil; paraffin, potato starch, polyethylene glycols (eg the Carbowaxes 3350® and 1450®, and Carbopol 934® of Union Carbide), polyoxyethylene alkyl ethers (eg. macrogol ethers such as cetomacrogol 1000), polyoxyethylene sorbitan fatty acid esters (eg. the commercially available Tweens® of ICI specialty chemicals), polyoxyethylene castor oil derivatives, polyoxyethylene sterates, polyvinylalcohol(PVA), polyvinylpyrrolidone(PVP), phosphates, 4-(1,1,3,3-tetramethylbutyl)phenol polymer with ethylene oxide and formaldehyde, (also known as tyloxapol, superione, and triton), all poloxamers and polaxamines (e.g., Pluronics F68LF®, F87®, F108® and tetronic 908® available from BASF Corporation Mount Olive, N.J.), pyranosides such as n-hexyl β-D-glucopyranoside, n-heptyl β-D-glucopyranoside; n-octyl-β-D-glucopyranoside, n-decyl β-D-glucopyranoside; n-decyl β-D-maltopyranoside; n-dodecyl β-D-glucopyranoside; quaternary ammonium compounds, silicic acid, sodium citrate, starches, sorbitan esters, sodium carbonate, solid polyethylene glycols, sodium dodecyl sulfate, sodium lauryl sulfate (e.g., Duponol P® of DuPont corporation), steric acid, sucrose, tapioca starch, talc, thioglucosides such as n-heptyl β-D-thioglucoside, tragacanth, triethanolamine, Triton X-200® which is a alkyl aryl polyether sulfonate (of Rhom and Haas); and the like. The inert diluents, solubilizing agents, emulsifiers, adjuvants, wetting agents, isotonic agents, colloidal dispersants and surfactants are commercially available or can be prepared by techniques know in the art. The properties of many of these and other pharmaceutical excipients suitable for addition to the process solvent streams before or after mixing are provided in Handbook of Pharmaceutical Excipients, 3rd edition, editor Arthur H. Kibbe, 2000, American Pharmaceutical Association, London, the disclosure of which is hereby incorporated by reference in its entirety.

Colloidal dispersants or surfactants can be added to colloidal mixtures such as a solution containing nanoparticles to prevent aggregation of the particles. In one embodiment of the invention, a colloidal dispersant is added to either the process solvent or non-process solvent prior to mixing. In one embodiment, the colloidal dispersant can include a gelatin, phospholipid or pluronic. The dispersant is typically added in a ratio up to 2:1 with the additive target molecule by weight. The use of a colloidal dispersant can prevent nanoparticles from growing to a size that makes them useless.

In another embodiment of the invention, the additive target molecule is mixed with the amphiphilic copolymer with a supplemental seeding molecule. The inclusion of a supplemental seed molecule in the process solvent facilitates the creation of nanoparticles upon micromixing with the non-process solvent. Examples of a supplemental seed molecule include, but are not limited to, a substantially insoluble solid particle, a salt, a functional surface modifier, a protein, a sugar, a fatty acid, an organic or inorganic pharmaceutical excipient, a pharmaceutically acceptable carrier, or a low molecular weight oligomer.

In one embodiment, a supplemental surfactant can be added to the process or non-process solvents. This process can be performed with amphiphilic copolymer alone or with amphiphilic copolymers containing an additive target molecule.

Nanoparticles

Preferably the nanoparticle compositions containing one or more amphiphilic copolymers, with or without one or more target molecules, and with or without one or more supplemental additives which are produced by a flash precipitation of the invention have an average size less than 1060 nm and more preferably less than about 700 nm, less than about 500, less than about 400, less than about 200, less than about 100, less than about 40 nm. The average size is on a weight basis and is measured by light scattering, microscopy, or other appropriate methods. Preferably at least 65% of the particles by weight have a particles size less than 1060 nm, and more preferably at least 80% of the particles are less than 1060 nm, and even more preferable at least 95% of the particles on a weight basis have a particle size less than 1060 nm as measured by light scattering, microscopy, or other appropriate methods.

Processing of Nanoparticle Compositions

The nanoparticles produced by the flash precipitation process can be post processed to yield a sterile aqueous or nonaqueous solution or dispersion or could be isolated, such as via lyophilization and autoclaving, to yield a sterile powders for reconstitution into sterile injectible solutions or dispersions. The nanoparticles can be combined with other acceptable compounds for parenteral injection such as but not limited to one or more of the following water, ethanol, propyleneglycol, polyethyleneglycol, glycerol, vegetable oils, ethyl oleate. Supplemental additives suitable suitable for parenteral injection can also be used to taylor the composition to that suitable for a specific purpose.

In one embodiment, nanoparticles are formed in the absence of a target molecule. The hydrophobic additive target molecule and optionally supplemental additives are added and the nanoparticles are loaded with a target molecule using differential partitioning where the solvent quality for the target molecule is slowly changed using dialysis or distillation. The resulting loaded particles are then isolated and used in a pharmaceutical formulation.

In one embodiment, the stream of nanoparticles produced via the flash precipitation, is distilled to remove any toxic solvents and sterile filtered using a 0.22 μm nominal pore size filter to yield a sterile solution. In another embodiment, the process solvent streams are sterilized prior to use and are flash precipitated in a sterile environment to produce a sterile formulation. Any post processing is also performed under sterile conditions.

The nanoparticulate compositions produced by the herein via flash precipitation may also contain supplemental additives useful for preserving, wetting, emulsifying, or dispensing the pharmaceutical composition. Prevention of the growth of microorganisms can be ensured by various antibacterial and antifungal agents, such as but not limited to sorbic acid, parabens, phenol, chlorobutanol. It may be desirable to add an antioxidant such as tocopherol or it may be desirable to include isotonic agents, such as sugars or sodium chloride.

In one embodiment, the nanoparticles formed via flash precipitation are isolated via distillation to remove toxic solvents such as THF, a supplemental additive is added, such as the cryoprotectant sucrose or trehelose, and the material is lyophilized to obtain a powder.

In one embodiment, the nanoparticle compositions produced by a flash precipitation of the invention are formulated into a solid dosage form for oral administration such as capsules, tablets, pills, powders, and granules. In such solid dosage forms, the nanoparticle composition is admixed with one or more supplemental additives falling into the following classes such as but not limited to lubricants, buffering agents, wetting agents, adsorbtion, inert excipients, binders, disintegrating agents, solution retarders, accelerators, adsorbents, or fillers or extenders or other components commonly used by those skilled in the art for production of solid dosage forms.

In one embodiment, nanoparticles created by flash precipitation are made comprising a exterior presenting a mucoadherent such as polyacrylic acid to the surface. Preferable that mucoadherent is part of a polybutylacrylate-b-polyacrylic acid amphiphilic copolymer. The particles are subsequently formulated as a delayed release method capable of presenting the mucoadherent to the lower gastrointestinal tract.

In one embodiment, the nanoparticle compositions is a potent pharmaceutical containing one or more amphiphilic copolymers, with or without one or more target molecules, and with or without one or more supplemental additives which are produced by a flash precipitation of the invention are made into a solid dosage form and due to its nanoparticulate size it is evenly dispersed throughout said solid dosage form admixture and yields a high content uniformity (quantity of material in each dose) not obtained if the drug was microparticulate.

In one embodiment, the nanoparticle compositions produced by a flash precipitation of the invention are formulated into a pharmaceutically acceptable liquid dosage form for oral administration such as a syrup, solution, emulsion, suspension, or elixir. In addition to the amphiphilic copolymer nanoparticulates, the liquid dosage forms may comprise inert diluents, solubilizing agents, oils, emulsifiers, adjuvants suspending agents, sweeteners, wetting agents, flavoring agents, perfuming agents or other compounds commonly used by those skilled in the art.

The nanoparticle compositions containing one or more amphiphilic copolymers, with or without one or more target molecules, and with or without one or more supplemental additives which are produced by a flash precipitation of the invention can be administered to humans and animals via a number of means including but not limited to orally, rectally, parenterally (intravenous, intramuscular, or subcutaneous), intracisternally, intravaginally, intraperitoneally, locally (in the form of powders, ointments or drops) or as a buccal or nasal spray.

Particle Functionalization

In another embodiment of the invention, pre-existing nano- or microparticles can be functionalized by treatment with an amphiphilic copolymer. In this embodiment, the pre-existing particle is dispersed in a solvent at a controlled temperature and pressure. An amphiphilic copolymer is dissolved in a solvent capable of mixing with the solvent containing the pre-existing particle but have different solubility characteristics for the amphiphilic copolymer. The two solutions are then mixed with a controlled temperature and mixing velocity causing selective precipitation of at least one amphilyte portion of the amphiphilic copolymer and at least one amphilyte portion of the same copolymer remains soluble through flash precipitation of the amphiphilic copolymer and the pre-existing particles. The resulting product contains particles that have been functionalized by flash precipitation with an amphiphilic copolymer. Preferably, the average size of the functionalized particle is within 30% of its initial size. The initial size of the particles can be <50 μm or over 2300 nm. In a preferred embodiment, the ratio of pre-existing particle to amphiphilic copolymer is 1:1. Pre-existing particles can be comprised of biologically or organically active compounds or precursors, anti-inflammatories, anti-depressants, anti-oxidants, proteins, water insoluble vitamins, agricultural actives or precursors, ceramics, latex, glass, or metal.

EXAMPLES

Some illustrative but non-limiting examples are provided hereunder for the better understanding of the present invention and for its embodiments.

For the examples containing a substantial fraction of nanoparticles <100 nm in diameter, photon correlation spectroscopy was performed on a Brookhaven with an ALV5000 multiple tau correlator to determine the average particle size using a second order cumulant fit. In accordance with standard practice, the viscosity and index of refraction of the solvent at a volume percentage the same as after mixing were input as properties of the fluid. A Malvern Mastersizer S version 2.18 was also used to determine the particle size distribution based on volume, or similar to a weight. Likewise, the average particle size was based on volume or mass, D[4,3]. The data analysis used a polydisperse model and the Standard-Wet (3OHD) presentation that assumes the particle is suspended in water. Some samples were diluted with water for analysis. For all processing conditions, the water used was purified by RO and filtered and the temperature is given within 2° C. The polymer blocks were nominal molecular weight with the nomenclature (1000) describing a block nominally of 1000 g/mole. The blocks could have contained minor impurities (<10% by weight and typically <5% by weight) due to the method of synthesis.

Example 1

Nanoparticles of Polystyrene-Block-Polyethylene-oxide ("PS(1000)-b-PEO(3000)") in Tetrahydrofuran ("THF") and Water Made in a Continuous Flash Mixer This example demonstrates the ability of the continuous flash mixer to produce nanoparticles that are <100 nm in diameter by controlling the mixing.

Figure 3:
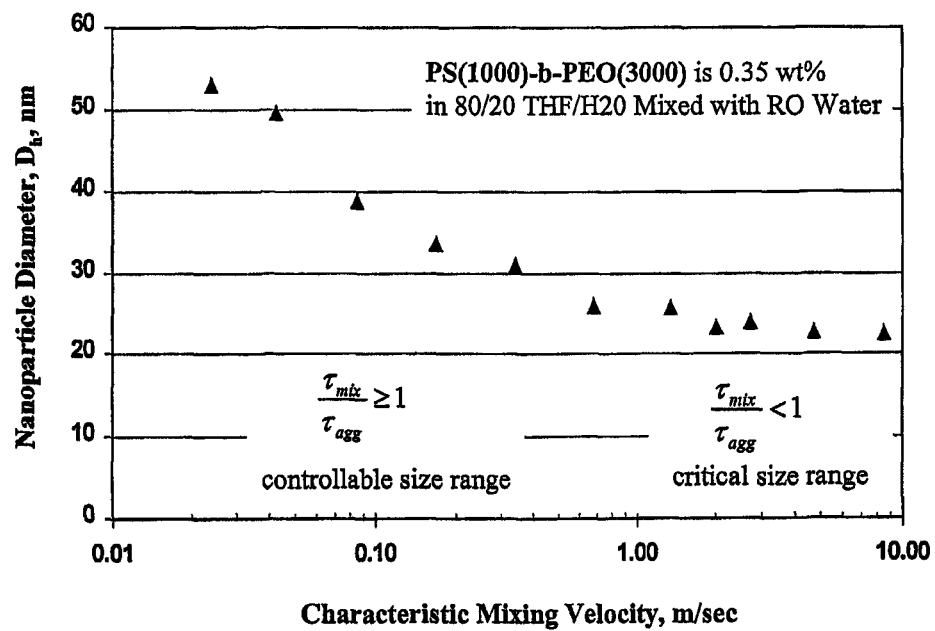
FIG. 3 is a graphic depiction of nanoparticle size in relation to the mixing velocity for nanoparticles formed from polystyrene(1000)-block-polyethyleneoxide(3000) ("PS(1000)-b-PEO(3000)") in tetrahydrofuran ("THF") and water in a continuous flash mixer. The ratios of mix time and aggregation time are also presented in relation to nanoparticle size.

A total of 0.71 grams of an amphiphilic block copolymer, PS(1000)-b-PEO(3000), was dissolved in 152 grams of tetrahydrofuran ("THF") and 48.4 grams of RO purified water. This mixture's concentration was 0.35 weight percent ("wt %") amphiphilic copolymer in THF containing 20 volume percent ("volume %") water. The solution was visually clear and free of particles. The solution was mixed at a 1:1 volume ratio with RO water entering from the second inlet in the continuous flash mixer of FIG. 1 with an inlet diameter of 0.5 mm and a conical outlet leading to a tube diameter of 1 mm. The two solvent streams were at 25° C. through the inlet tubes. The size of the nanoparticles created by this process were controlled by adjusting the average velocity of the incoming stream between about 0.02 and 8.5 meters per second as shown in FIG. 3. Mean particle size was observed to be between about 22 nm and 55 nm depending on mixing velocity, with smaller particles resulting with higher mixing velocities. Several milliliters of the process stream exiting the mixer at each operating condition were collected in a sample vial for analysis by photon correlation spectroscopy. Several samples at both high and low mixing rates were assayed after a period of two weeks and shown to have a size within 6 nm of their original size, indicating a stable particle size.

Example 2

Nanoparticles of PS(1000)-b-PEO(3000) and β-Carotene in a 1:1 Ratio in THF and Water Made in a Continuous Flash Mixer This example demonstrates that a pharmaceutical compound, an antioxidant and a vitamin useful for mammal administration, can be formulated as nanoparticles using amphiphilic copolymers and a continuous flash mixer to yield a surface of PEO groups. This example also demonstrates that the nanoparticles produced by flash precipitation are sufficiently stable for post processing and subsequent formulation. One hundred percent of the particles were less than 700 nm and the average particle size was less than 400 nm.

A total of 3.32 grams of β-carotene, an additive target molecule, and 3.32 grams PS(1000)-b-PEO(3000) were dissolved in 123 grams of THF at 35° C. These charges correspond to 2.6 wt % copolymer, 2.6 wt % β-carotene and a weight ratio of 1:1 for amphiphilic copolymer to additive target molecule. The solution was a deep red color and visually clear of particles. The process solvent stream was mixed with water, entering from the second inlet at a volume ratio of 1:0.94 in the continuous flash mixer at a temperature of 35° C. Both streams entered the mixer through tubes 1 mm in diameter. The diameter of the mixing vessel was 4.8 mm and the outlet was conical leading to an outlet tube 2 mm in diameter. The average velocity of the β-carotene stream was 2.8 m/s corresponding to a total solids (when dried) production rate of over 9 kg/day, or a liquid processing rate (both streams) of over 340 kg/day. The total solids concentration of the mixer effluent after nanoparticle formation was approximately half the original value, or 2.6 wt %.

Figure 4:
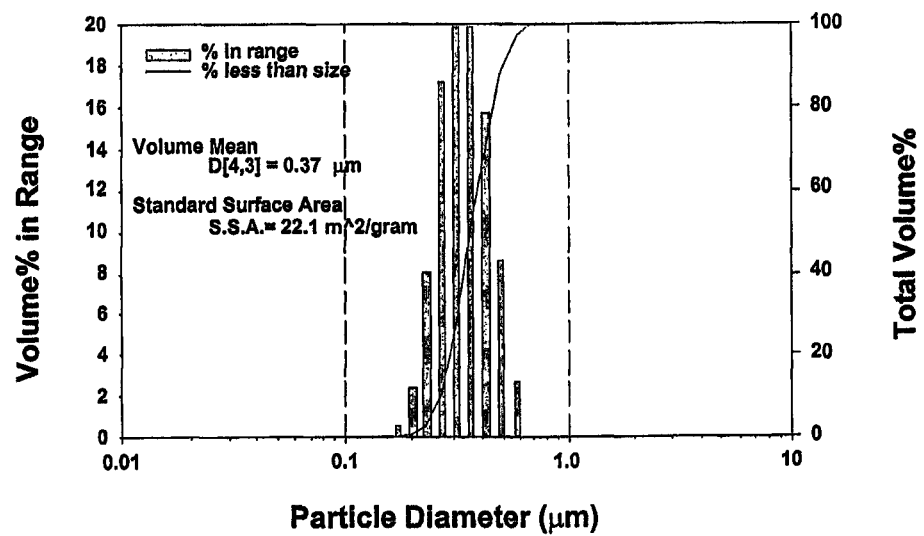
FIG. 4 is a graphic depiction of volume percentage of nanoparticles by the distribution of nanoparticle size for nanoparticles formed from PS(1000)-b-PEO(3000) in THF and water in a continuous flash mixer and containing the additive target molecule, β-carotene, in a 1:1 ratio with copolymer where copolymer and additive were both 2.6 wt %.

In a period of approximately 20 seconds, 90.5 grams of nanoparticle product effluent from the continuous flash mixer was collected in 444 grams of agitating RO water and a well agitated sample was diluted further with water to a concentration suitable for analysis. The yield of nanoparticles below 1060 nm was 100% with a mean size of 0.37 μm as measured by a Malvern Mastersizer S. The particle size distribution of this example is shown in FIG. 4. The product was opaque and orange and no large particles were distinguishable by eye in any of the samples diluted for analysis or in the product stream. Three weeks later, a second sample of the collected product stream was agitated and diluted further with water and analyzed. The yield of nanoparticles below 1060 nm was over 99% as measured by a Malvern Mastersizer S with a mean size of 0.42 μm.

Example 2A

Nanoparticles of PS(1000)-b-PEO(3000) and β-Carotene in a 1:1 Ratio in THF and Water Made in a Continuous Flash Mixer A total of 4.6 grams of β-carotene and 4.6 grams PS(1000)-b-PEO(3000) were dissolved in 166 grams of THF at 35° C., corresponding to 2.6 wt % copolymer, 2.6 wt % β-carotene, and a weight ratio of 1:1 for amphiphilic copolymer to additive target molecule. The solution was a deep red color and visually clear of particles. The process solvent stream was mixed with water, entering from the second inlet, at a volume ratio of 1:0.94 in the continuous flash mixer at a temperature of 35° C. (see FIG. 1). Both streams passed through the coil heat exchanger and entered the mixer through a 1 mm-tube. The pressure of the incoming streams were controlled at 17 psig., and the receiver was at atmospheric pressure. The mixer chamber diameter was 4.8 mm and the outlet was conical leading to an outlet tube of 2 mm. The average velocity of the process solvent stream was 4.3 m/s corresponding to a liquid processing rate of over 500 kg/day and a total solids when dried production rate of over 13 kg/day. The total solids concentration of the mixer effluent after nanoparticle formation was approximately half the original value, or 2.6 wt % and comprised 50% β-carotene.

In a period of approximately 10 seconds, 85 grams of nanoparticle product effluent from the continuous flash mixer was collected in 488 grams of RO water in a separate holding tank and a well agitated sample was diluted further with water to a concentration suitable for analysis. The yield of nanoparticles below 1060 nm was 100% with a mean size of 0.36 μm as measured by a Malvern Mastersizer S. The product was opaque and orange and no large particles were distinguishable by eye in any of the samples diluted for analysis or in the product stream. Three months later without agitation in between, a second agitated sample of the collected product stream was taken and diluted further with water and analyzed. The yield of nanoparticles below 1060 nm was 100% as measured by a Malvern Mastersizer S with a mean size of 0.40 µm. This result indicated the sufficient stability of the nanoparticles was achieved to conduct additional post processing steps.

Example 2B

Post Processing Treatment of Nanoparticles of PS(1000)-b-PEO(3000) and β-Carotene This example demonstrates a post processing process useful for the formulation of target molecules of a pharmaceutical for administration as a liquid.

Figure 5:
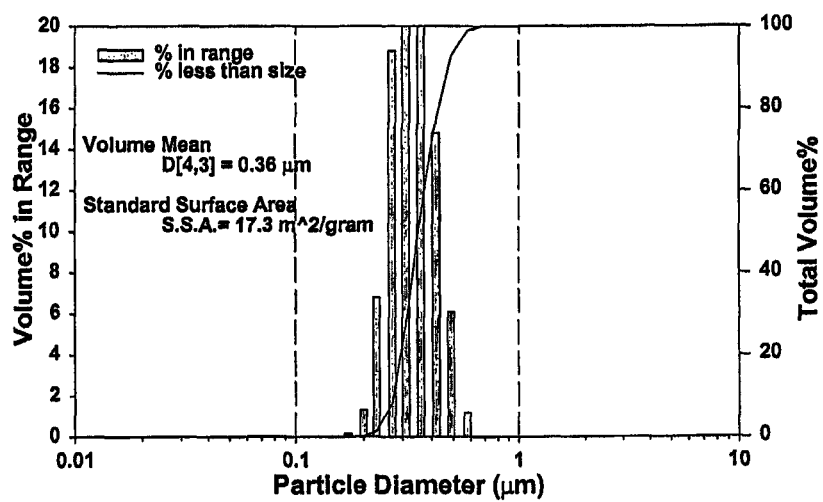
FIG. 5 is a graphic depiction of volume percentage of nanoparticles by the distribution of nanoparticle size for nanoparticles formed from PS(1000)-b-PEO(3000) in THF and water in a continuous flash mixer and containing the additive target molecule, β-carotene, in a 1:1 ratio with copolymer after removal of organic solvent where copolymer and additive were both 2.6 wt %.

Approximately, half the effluent collected in Example 2A, 305 g, was distilled under reduced pressure at a temperature less than 70° C. A total of 3.3 volumes of RO water was added portion-wise in four parts bringing the concentration to the starting value prior to the next addition. The final concentration was the same as the original and the resulting particle size distribution of this example was measured the next day with results as shown in FIG. 5. The yield of nanoparticles below 1060 nm was 100% with a mean size of 0.36 µm as measured by a Malvern Mastersizer S and with a average size less than 400 nm.

Example 2C

Filtration and Lyophilization of Nanoparticles

A 1.2 µm (nominal) nylon syringe filter was dried under vacuum at 80° C. A portion of the nanoparticle product of example 2B, after the post processing treatment to remove solvent and after aging the material at room temperature for 11 weeks in a sealed bottle in a quiescent state, was agitated and filtered through the same 1.2 µm nylon filter at room temperature followed by a RO water wash of 0.18 volumes. A total of 177 mg of sucrose was added to the filtrate and the combination was lyophilized to obtain 300 mg of a solvent and aqueous free powder. Meanwhile, the filter was again dried under vacuum at 80° C. and less than 1 mg of product was caught on the filter, less 1% of the nanoparticles present. No microparticles were visible to the eye on the filter. A sample of the filtrate after the addition of sugar analyzed by the Mastersizer S showed essentially the same particle size as measured previously; 100% of the particles were <1060 nm in diameter and had a mean size of 0.36 µm.

Example 3

Nanoparticles of PS(1000)-b-PEO(3000) and β-Carotene in a 1:6.5 Ratio in THF and Water Made in a Continuous Flash Mixer Several nanoparticle solutions were prepared from process solvent containing 0.40 wt % PS(1000)-b-PEO(3000) and 2.6 wt % β-carotene copolymer with a weight ratio of 1:6.5 for amphiphilic copolymer to additive target molecule in THF at 35° C. using water as the non-process solvent. The mixing velocities for each process are presented in Table 1 below. Final nanoparticle solutions were diluted in water and agitated for measurement.

The total solids concentration of the mixer effluent after nanoparticle formation was 1.5 wt %. The nanoparticle product stream was added to RO water in the agitated vessel at a ratio of 1:4 to 1:6. This mixture was then diluted again with water to a concentration appropriate for particle size analysis using the Mastersizer S.

TABLE 1

| β-carotene (g) | PS(1000)-b-PEO(3000) (g) | ratio | THF (g) | Mixing Velocity (m/sec) | Liquid Product (g) | H$_2$O (g) |
|---|---|---|---|---|---|---|
| 2.72 | 0.416 | 6.54 | 102 | 0.30 | na | 160 |
| 2.4 | 0.36 | 6.67 | 88 | 0.90 | 82.6 | 444 |
| 2.72 | 0.416 | 6.54 | 102 | 1.27 | 43.3 | 160 |
| 2.83 | 0.44 | 6.40 | 108 | 1.70 | 95.6 | 444 |
| 4.93 | 0.753 | 6.55 | 184 | 2.84 | 86.5 | 444 |
| 6.18 | 0.96 | 6.44 | 231 | 4.27 | 52.6 | 248 |
| 6.18 | 0.96 | 6.44 | 231 | 4.27 | 26.15 | 175 |

The average velocity of the stream containing the copolymer and target molecule was between about 0.9 to 4.3 m/sec and the resulting nanoparticles characteristics are displayed in FIG. 5 with most particles displaying an average diameter of <0.5 µm and all particles having an average diameter of <1.0 µm. The nanoparticle production rate (dry solids content) reached over 7.5 kg/day and the fluid processing rate exceeded 500 kg/day. The total solids concentration of the mixer effluent after nanoparticle formation was approximately half the original value, or 1.5 wt % and comprised 85% target molecule by weight.

Figure 6:
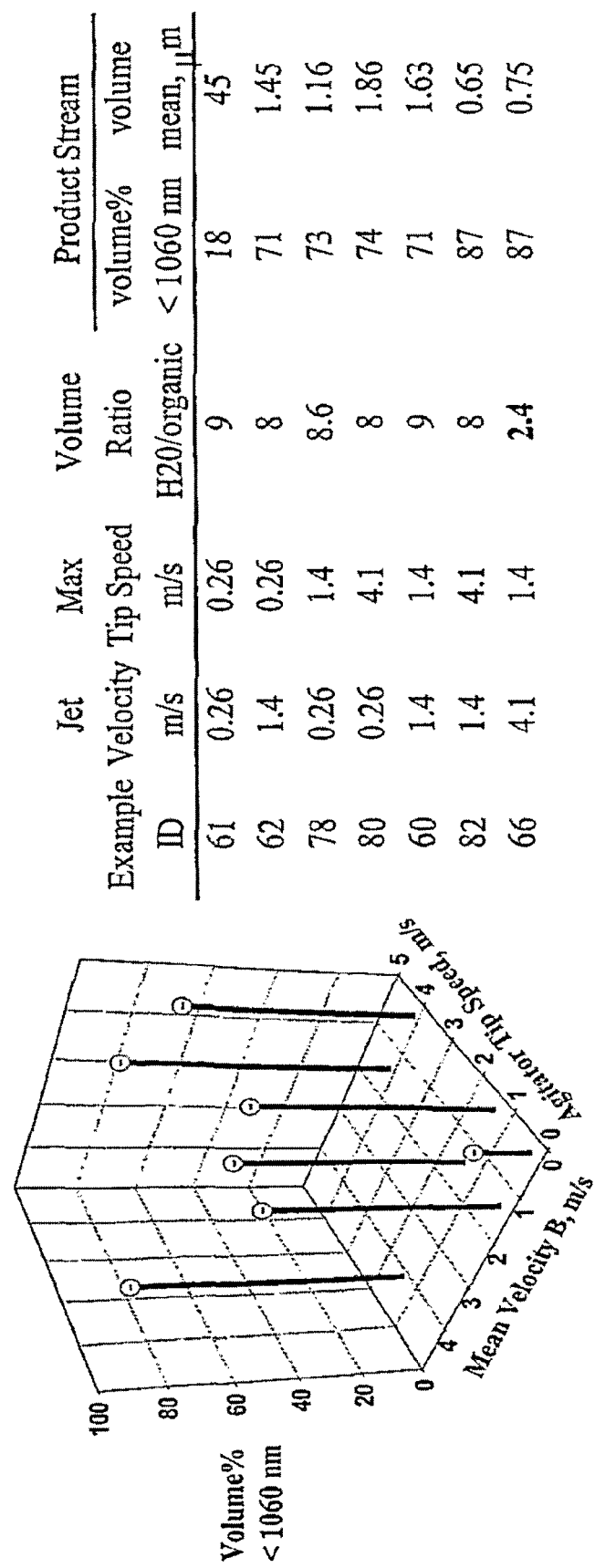
FIG. 6 is a graphic depiction of volume percentage of nanoparticles in relation to mean velocity and agitator tip speed for nanoparticles formed from PS(1000)-b-PEO(3000) in THF and water in a batch flash mixer and containing the additive target molecule, β-carotene, in a 6.5:1 ratio with copolymer.

Higher velocities produced higher yields of nanoparticles or a smaller nanoparticle size as shown in FIG. 6. The stability of the run at a velocity of 4.3 m/sec was tested two weeks later and found to be acceptable for post processing, a total of 91% of the particles were less than 1060 nm in diameter. These examples demonstrate sparing quantities of the amphiphilic copolymer can be used to afford the desired nanoparticle production.

Example 3B

Nanoparticles of PS(1000)-b-PEO(3000) and β-Carotene in a 1:6.5 Ratio in THF and Water Made in a Continuous Flash Mixer The conditions of Example 3 were the same except that the mixing velocity was 0.30 m/s. At this velocity, the mixer plugged with particles since the particles were formed at a size a large fraction of particles were formed at a size significantly larger than 1 µm.

Example 4

Nanoparticles of PS(1000)-b-PEO(3000) and β-Carotene in a 1:6.5 Ratio in THF and Water Made in a Batch Flash Mixer The purpose of this example was to demonstrate a flash mixer in a batch configuration could be used to create nanoparticles of a poorly water-soluble pharmaceutical compound useful for administration to mammals. The example was also conducted to demonstrate the mixing velocity for the flash precipitation can be represented by a moving surface.

The THF solvent stream contained dissolved 0.40 wt % PS(1000)-b-PEO(3000) copolymer and 2.6 wt % β-carotene, a weight ratio of 1:6.5:1 for amphiphilic copolymer to additive target molecule. The process solvent was fed from a syringe pump through a coiled stainless steel tube 1/8th inches in diameter and submersed in a water bath at 35° C. Within 10 inches after exiting the bath, the tube entered the mixing vessel containing RO water and was connected to a tube 1 mm in diameter tube below the water surface. The process solvent was fed into the zone of high intensity of the mixing vessel within 3 mm of a mechanical agitator.

Figure 7:
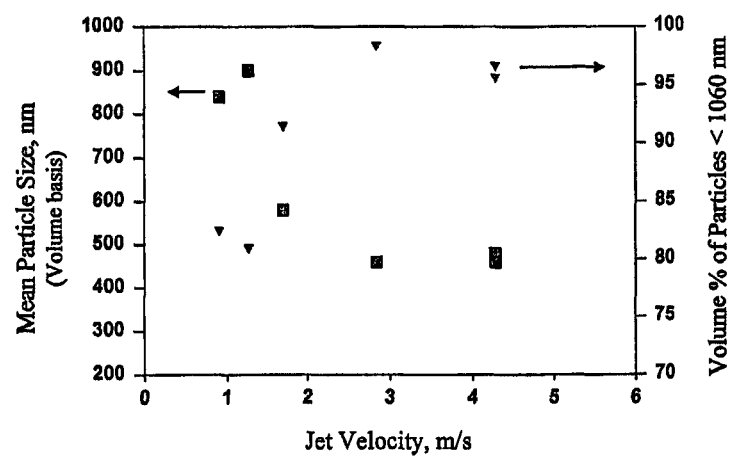
FIG. 7 is a graphic depiction of mean nanoparticle size in relation to the jet velocity for nanoparticles formed from PS(1000)-b-PEO(3000) in THF and water in a continuous flash mixer and containing the additive target molecule, β-carotene, in a 6.5:1 ratio with copolymer.

The fluid jet velocity of the process solvent exiting the inlet tube was varied between 0.26 m/s and 4.1 m/s and the mechanical agitator tip speed was varied between 0.26 m/s and 4.1 m/s. Each combination of jet velocity and tip speed is presented in FIG. 6 with the greatest volume percent of particles having a diameter of <1060 nm when the jet velocity and agitator tip speed were high. The organic stream was charged to 180 grams of RO water at 35° C. to a volume ratio with the exception of Example ID 62 in which the charge was 128 grams. The data in FIG. 7 was collected by further dilution of the batch product stream to that appropriate for analysis by the Mastersizer S. At the lowest mixing velocity evaluated, 0.26 m/sec, 18% of the particles were less than 1060 nm in diameter. All other mixing velocities produced more than 65 volume % of particles less than 1060 nm with the greatest amount of particles less than 1060 nm at 87 volume % and a volume mean size of 0.65 µm. A high ratio of additive target molecule to amphiphilic copolymer was used and the product stream can be produced at a high concentration (0.9 wt % solids on a dry basis of which over 85% was target molecule as shown in Example ID 66).

As with the continuous flash mixer, a threshold mixing velocity is required to ensure that over 65% of the nanoparticles by volume are less than 1060 nm in diameter. In addition, the mixing velocity of the agitator and the fluid jet velocity can affect the volume % of nanoparticles that are less than 1060 nm. For equipment agitated by mechanical means, the mixing velocity characteristic of the moving surfaces provides a rapid mixing time and causes flash precipitation.

Example 5

β-Carotene in THF with no Amphiphilic Copolymer

Two solutions of THF were made with 2.6 wt % β-carotene. One solution contained THF and β-carotene only and the other contained 0.4 wt % of a common surfactant, the poloxamer, F87® (polyoxypropylene/polyoxyethylene available from BASF), of the type used for pharmaceutical applications. The average jet velocity was 1.4 m/s and the agitator tip speed was 1.4 m/s for both solution examples. The process solvent was charged through a 1 mm tube, within 3 mm of the agitator, to 180 grams of RO water at 35° C. or 38° C., and to a volume ratio of 8:1 non-process solvent to process solvent. In the absence of any copolymer or surfactant, only 9% of the β-carotene particles were less than 1060 nm and the volume mean was 120 µm. Addition of the surfactant, F87, produced only 18% of the particles with a diameter of less than 1060 nm with a mean size of 140 µm.

As demonstrated by average particle size greater than 100 µm, using common surfactants or without using any additive, did not constitute a flash precipitation to produce a high yield of nanoparticles.

Example 6

PS(1000)-b-PEO(3000) and β-Carotene in a 1:6.5 Ratio in THF and Water Using Conventional Mixing A THF solvent stream contained dissolved 0.40 wt % PS(1000)-b-PEO(3000) copolymer and 2.6 wt % β-carotene with a weight ratio of 1:6.5 for amphiphilic copolymer to additive target molecule. The process and non-process solvents were mixed by conventional means at 33° C., by pouring a total of 19.8 grams of the process solvent into 182 grams of RO water in a beaker with moderate agitation (magnetic stirrer, near 30 mm, at approximately setting of 4.3 on a scale of 1-6). The final volume ratio was 1:8.3 for process solvent to water. Mixing was completed in 20 seconds. A sample of the batch was withdrawn and diluted with water to a concentration appropriate for particle size analysis. The yield of nanoparticles less than 1060 nm was 46% based on the Mastersizer S analysis. In both the final mixture and samples diluted for analysis, large particles were distinguishable by eye.

As demonstrated by this example, conventional means of mixing are limited in their ability to produce nanoparticles containing target molecules.

Example 7

Nanoparticles of Polybutylacrylate(7500)-b-Polyacrylicacid(7500) ("PBA(7500)-b-PAA(7500)") in Methanol ("MeOH") Precipitated with MeOH/Water in a Continuous Flash Mixer This example demonstrates the production of nanoparticles of amphiphilic copolymers where the soluble exterior surface constitutes a mucoadherent and the formed nanoparticles. The concentration of amphiphilic copolymer was increased and still produced a consistent and controllable size of nanoparticles when a commensurate increase in the mixing velocity was imposed.

Solutions of MeOH containing the amphiphilic block copolymer PBA(7500)-b-PAA(7500) were prepared at a concentrations ranging from of 0.10 to 0.65 wt %. At 35° C., the solutions were visually clear and free of particles. The solutions were mixed with either water or a water/MeOH mix at 35° C. using a continuous flash mixer. The process and non-process solvents were fed through thin walled stainless steel tubing 1/8th inches in diameter and coiled in a water bath and to the mixer of FIG. 1 with tube diameters of 0.5 mm, D/d of 4.8 and δ/d of 2.

The resulting average nanoparticle size was dependent on the mixing velocity and ranged from about 25 nm to about 60 nm for nanoparticles precipitated with water and from about 35 nm to 65 nm for nanoparticles precipitated with a water/MeOH non-process solvent. The distribution of nanoparticle size based on mix velocity and mean particle size is presented in FIG. 8 and FIG. 9. At the highest velocity, a critical process was obtained and the smallest nanoparticles were produced. The resulting particles were stable, changing in size less than 6 nm over a period of 3 months.

Example 7A

PBA(7500)-b-PAA(7500) in MeOH Precipitated with Water Using Conventional Means

Figure 8:
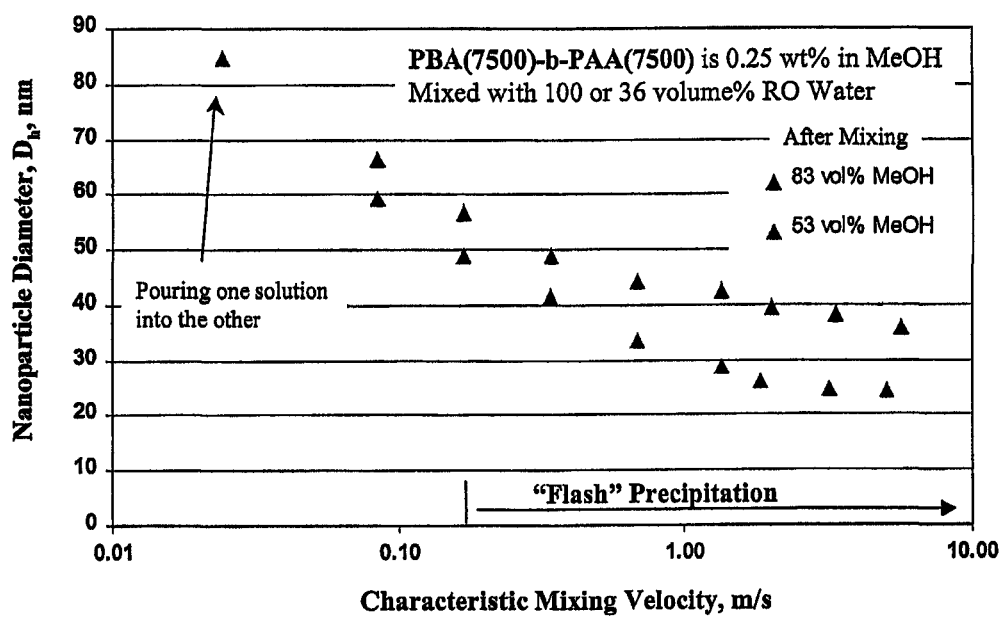
FIG. 8 is a graphic depiction of nanoparticle size in relation to the mixing velocity for nanoparticles formed from polybutylacrylate(7500)-b-polyacrylicacid(7500) ("PBA(7500)-b-PAA(7500)") in methanol ("MeOH") and MeOH/water in a continuous flash mixer for samples with having volume % MeOH of 83% and 56% in the initial mixture.
Figure 9:
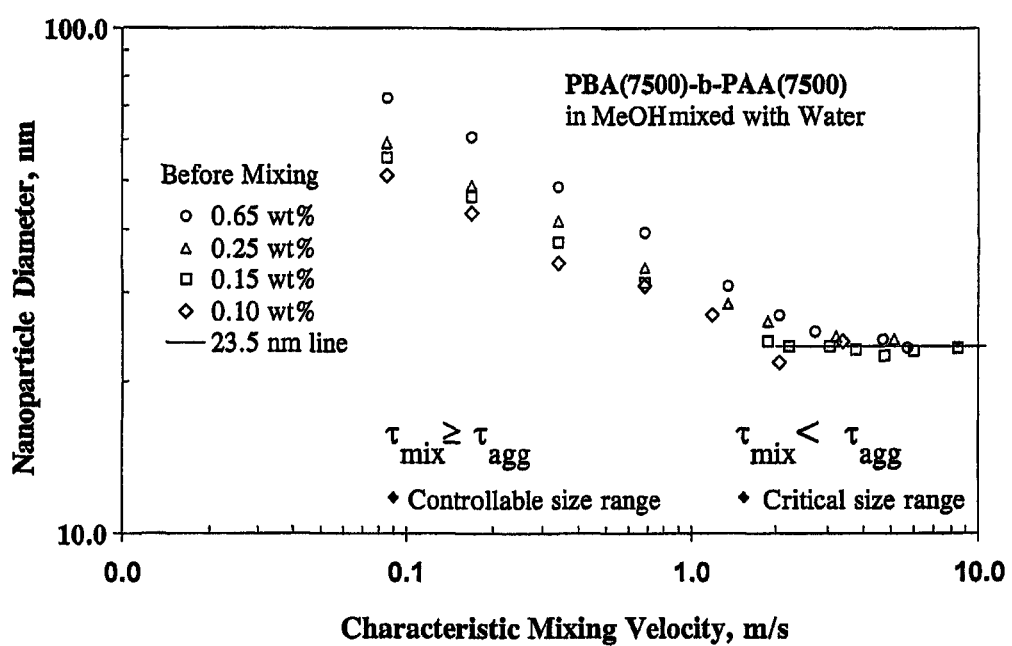
FIG. 9 is a graphic depiction of nanoparticle size in relation to the mixing velocity for nanoparticles formed from PBA(7500)-b-PAA(7500) at varying weight percentage (wt %) concentration of copolymer before mixing in MeOH and water in a continuous flash mixer; threshold mixing times and aggregation times are also presented in relation to nanoparticle size.

The same 0.25 wt % solution of PBA(7500)-b-PAA(7500) mixed with water and MeOH using conventional means. A total of 1.66 grams of PBA(7500)-b-PAA(7500) was mixed with 1.76 g of 64.5% methanol and water, a ratio of 1:0.93 by volume. The methanol and water were poured into the flask containing the copolymer and mixed with moderate agitation by hand. The resulting nanoparticles had an average diameter of 85 nm as shown in FIG. 8.

As demonstrated by the example, conventional mixing did not form nanoparticles at the size and yield obtained in the continuous flash mixer.

Example 8

Nanoparticles of Polybutylmethacrylate(1000)-b-Polyethyleneoxide(3000) ("PBMA(1000)-b-PEO (3000)") and β-Carotene in a 1:1 Ratio in THF and Water Made in a Continuous Flash Mixer A total of 4.6 grams PBMA(1000)-b-PEO(3000) and 4.6 grams of β-carotene were dissolved at 35° C. in 166 grams of THF. These charges correspond to 2.6 wt % copolymer, 2.6 wt % β-carotene and a weight ratio of 1:1 for amphiphilic copolymer to additive target molecule. The solution was a deep red color and visually, clear of particles. The process solvent stream was mixed with water, entering from the second inlet, at a volume ratio of 1:0.94 in the continuous flash mixer at a temperature of 35° C. Both streams passed through the coil heat exchanger and entered the mixer through a 1 mm-tube. The pressure of the incoming streams were controlled at 9 psig., and the receiver was at atmospheric pressure. The mixer chamber diameter was 4.8 mm. In a period of approximately 10 seconds, 55 grams of effluent were collected in 304 grams of RO water. The resulting nanoparticles of organic active were 97%<1060 nm with a average or mean size D[4,3] of 0.45 μm.

Example 9

Nanoparticles of PS(1000)-b-PEO(3000) and β-Carotene in THF and Water Made in a Centripetal Mixer A solution of 0.4 wt % PS(1000)-b-PEO(3000) copolymer and 2.6 wt % β-carotene in THF was made with 0.73 g PS(1000)-b-PEO(3000), 4.75 g β-carotene, and 178 g THF with a weight ratio of 1:6.5 for amphiphilic copolymer to additive target molecule. The process solvent stream was mixed with water at 35° C., both of which were adjusted to 35° C. using a coil heat exchanger and through inlets of similar dimensions. The streams were introduced at a volume ratio of 1:3.0 to 1.6.0 process to non-process solvent in three separate mixing experiments in the centripetal mixer pictured in FIG. 10. A syringe pump was used for the process stream which was delivered at a pressure of 2.5 or 4.5 psig. The non-process solvent, RO water, was supplied to the centripetal mixer from a pressurized vessel delivered to the mixer at a pressure of 20-21 psig. The velocity of the process solvent stream entered at a mean velocity of 0.24 m/s to 0.44 m/s and the non-process stream entered at a mean velocity of 1.3 m/s.

In this mixer, the streams do not collide but are stretched as they circulate and eventually pushed through the exit hole in the bottom of the mixer. The ratio of dimensions in the mixer was D/δ=4, H/δ=1 and w/δ=0.8 representing a highly confined mixer. For each mixture, a portion of the effluent stream out of the mixer was collected in a receiving vessel consisting of an empty bottle. The product was opaque and orange and no large particles were distinguishable by eye.

Analysis several hours later by the Mastersize S showed a yield of 89 to 87% of the particles by volume were <1060 nm and the mean particle size was D[4,3]=0.6 μm.

Figure 10:
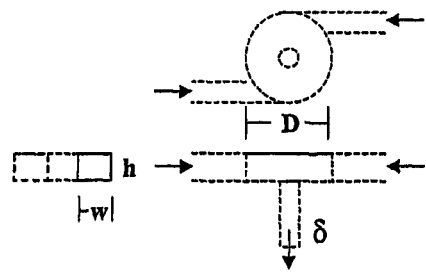
FIG. 10 is a schematic diagram of a centripetal flash mixer with mix velocities and nanoparticle production by volume percentage.

As shown in FIG. 10, a number of flow ratios can be used to produce a similar yield and average size of nanoparticles. Although the mixing velocity of the process solvent was changed, the non-solvent mixing velocity was held constant and the particles size was controlled by the velocity of the higher velocity stream. Likewise, in a confined mixer, the stream need not directly impact each other to obtain a good yield of nanoparticles.

Example 10

Nanoparticles of PS(1000)-b-PEO(3000) and β-Carotene in a 1:6.5 Ratio in THF and Water Made in a Continuous Flash Mixer Final Product Mixed with and without Sodium Dodecyl Sulfate ("SDS")

This example demonstrates that the addition of supplemental additives into the nanoparticle product stream can enhance the resulting product properties, such as long term stability of the particles.

Two separate vessels were attached to a continuous flash mixer to collect the nanoparticles produced from a flash precipitation of β-carotene and PS(1000)-b-PEO(3000) in THF and water. A total of 248 g of RO water was placed in one holding vessel and a total of 175 grams of RO water and 0.87 grams of a supplemental additive useful for post treatment, SDS (Sigma), was placed in a separate holding vessel.

A total of 0.96 g PS(1000)-b-PEO(3000) and 6.18 grams of β-carotene and were dissolved in 231 g of THF at 35° C., corresponding to 0.4 wt % copolymer, 2.6 wt % β-carotene and a weight ratio of 1:6.5 for amphiphilic copolymer to additive target molecule. The solution was a deep red color and visually clear of particles. The volume ratio of process solvent to non-process solvent was 1:0.94 for each mixture and both solvents were held at a temperature of 35° C.

Both the process and non-process solvent streams passed through the coil heat exchanger and entered the mixer through a tube of 1 mm. The pressure of the incoming streams were controlled at an average of 17 psig. and the mixing vessel was at atmospheric pressure. The mixing vessel diameter was 4.8 mm and the outlet was conical leading to an outlet tube of 2 mm and then to a transport tube of ⅛" Teflon for 8 inches before emptying into a product collection receiver. The average velocity of the process stream was 4.3 m/s. The total solids concentration of the mixer effluent after nanoparticle formation was approximately half the original value, or 1.5 wt % and comprised 85% target molecule by weight.

In a period of approximately 10 seconds, 52.6 grams of nanoparticle product effluent was collected from the continuous flash mixer into containing RO water only while agitating the contents. A well agitated sample was diluted further with water to a concentration suitable for analysis. The yield of nanoparticles below 1060 nm was 96% as measured by a Malvern Mastersizer S (volume %). The product was opaque and orange and no large particles were distinguishable by eye in any of the samples diluted for analysis or in the product stream. Fifteen days later, a second agitated sample of the collected product stream was taken and diluted further with water and analyzed. The yield of nanoparticles below 1060 nm was 91% as measured by a Malvern Mastersizer S.

Immediately after collecting nanoparticles in Vessel 1, a total of 26.15 grams of nanoparticle were collected into the holding vessel containing SDS and RO water. A well agitated sample was diluted further with water to a concentration suitable for analysis. The yield of nanoparticles below 1060 nm was essentially the same, 97% as measured by a Malvern Mastersizer S (volume %), as that collected in Vessel 1. The product was opaque and orange and no large particles were distinguishable by eye in any of the samples diluted for analysis or in the product stream. Fifteen days later, a second agitated sample of the collected product stream was taken and diluted further with water and analyzed. The yield of nanoparticles below 1060 nm was still 97% as measured by a Malvern Mastersizer S.

Example 11

Nanoparticles of PS(1000)-b-PEO(3000) and β-Carotene in a 2:1 Ratio in THF and Water Made in a Continuous Flash Mixer This example demonstrates a high yield of nanoparticles when the ratio of amphiphilic copolymer to target molecule is over 1:1 and the quantity of target molecule in the product stream on a dry weight basis can be adjusted over a wide range.

Two separate vessels were prepared to collect the nanoparticles stream from the continuous flash mixer. A total of 332 g of RO water was placed in one vessel and a total of 162 grams of RO water was placed in the other.

A total of 3.93 g PS(1000)-b-PEO(3000) were dissolved in 69.7 g of THF at 35° C. to visually clear state, then a total of 1.95 grams of β-carotene was added to this mixture, corresponding to 5.2 wt % copolymer, 2.6 wt % β-carotene, and a weight ratio of 2:1 for copolymer to β-carotene. The solution was a deep red color and visually clear of particles. The process solvent was mixed with water, entering from the second inlet, at a volume ratio of 1:0.96 in the continuous flash mixer at a temperature of 35° C. Both streams passed through the coil heat exchanger and entered the mixer through a tube of 1 mm. The mixer chamber diameter was 4.8 mm and the outlet was conical leading to an outlet tube of 2 mm. The average velocity of the β-carotene stream during the run was 2.8 m/s. The total solids concentration of the mixer effluent after nanoparticle formation was approximately half the original value, or 3.9 wt % and comprised 33% target molecule by weight.

In a period of approximately 10 seconds, 43 grams of nanoparticles from the continuous flash mixer were collected in 332 grams of RO water in a separate holding tank and agitated. A sample of this solution was diluted further with water to a concentration suitable for analysis. The yield of nanoparticles below 1060 nm was 100% with a mean size of 0.34 µm as measured by a Malvern Mastersizer S. The product was opaque and orange and no large particles were distinguishable by eye in any of the samples diluted for analysis or in the product stream.

Comparing this example to Example 1 and Example 3, it is apparent that nanoparticles can be made over a wide range of amphiphilic copolymers to target molecule, 0%, 33%, and 85% target molecule in the product stream on a dry solids basis was demonstrated.

Example 11A

Nanoparticles of PS(1000)-b-PEO(3000) and β-Carotene in a 2:1 Ratio in THF and Water Made in a Continuous Flash Mixer

Effect of Mixing Time

Immediately after collecting the sample for Example 11, the ratio of mixing for process and no-process solvent streams was changed to 1:0.93 and the velocity of the process solvent was also changed to 0.42 msec with all other conditions the same. A total of 28.5 grams of nanoparticle product was collected from the continuous flash mixer in 162 grams of RO water in a separate holding tank and was agitated. A sample was diluted with water to a concentration suitable for analysis. The yield of nanoparticles below 1060 nm was 93% with a mean size of 0.52 µm as measured by a Malvern Mastersizer S. The product was opaque and orange and no large particles were distinguishable by eye in any of the samples diluted for analysis or in the product stream. This example shows that the mixing velocity can control the particle size distribution.

Example 12

Nanoparticles of PS(1000)-b-PEO(3000) and β-Carotene Made in a Continuous Flash Mixer to Produce Nanoparticles <200 nm This example demonstrates nanoparticles of an amphiphilic copolymer and a pharmaceutical target molecule can form nanoparticles with an average size well below 200 nm and even below 100 nm. It also demonstrates that the mixing velocity can control the particle size and the particles are sufficiently stable for post processing.

Three vessels were connected to a continuous flash mixer and filled with 332 g, 162 g, 124 g of RO water, respectively for dilution of the product stream prior to analysis.

A total of 0.49 g PS(1000)-b-PEO(3000) and 0.49 g of β-carotene were dissolved in 92 g of THF at 25° C., corresponding to 0.53 wt % copolymer and 0.53 wt % β-carotene and a weight ratio of 1:1. The solution was a red color and visually clear of particles. The process stream was mixed with water, entering from the second inlet, at a volume ratio of 1:0.96, 1:0.93 and 1:0.93, respectively, into the continuous flash mixer of FIG. 1. Both the process solvent and non-process solvent streams were maintained at 35° C. The total solids concentration of the mixer effluent after nanoparticle formation was approximately half the original value, or 0.26 wt % and comprised 50% β-carotene.

One immediately after the other, the average velocity of process stream was changed from 2.8 m/s to 1.3 m/s to 0.42 m/s and the water stream was changed commensurately to maintain a ratio of 1:0.96, 1:0.93 and 1:0.93, respectively. A portion of the effluent, 42.6 g, 24.8 g, 26.7 g at each of these velocities were collected in separate vessels. The particle size distribution was too small to obtain reliable results with a Mastersizer S. The resulting particle size was analyzed by photon correlation spectroscopy yielding a nanoparticle size of 90 nm, 110 nm, and 160 nm in diameter, respectively. All samples were light orange, opalescent, and clear to the eye without any large particles present, consistent with particles less than 200 nm in size. Seven days later, the samples had essentially the same particle size, within 4%, as after formation.

Example 13

Nanoparticles of PS(1000)-b-PEO(3000) and β-Carotene with Lecithin and Sterile Filtered (Ntbk PM4-1C)

This example demonstrates the formation of nanoparticles of an amphiphilic copolymer and a pharmaceutical target molecule with a supplemental additive and purified by filtration.

A total of 0.164 g of lecithin (Epikuron™ 200), a phospholipid additive of the type commonly used in parenteral injections or liquid formulations, was added to 102 g of THF. The material dissolved to a visually clear solution of a pale yellow color. A total of 0.40 gPS(1000)-b-PEO(3000) copolymer and 0.56 g of β-carotene were added to the solution and dissolved at room temperature to a clear red solution free of particles. This process solvent stream containing an additive in addition to an amphiphilic copolymer with the target molecule was loaded into 100 mL syringes. RO water was also loaded into a separate set of 100 mL syringes. The two solutions were mixed at a ratio of 1:0.95 for process solvent to process non-solvent in a continuous mixer of the style in FIG. 1, with inlet tubes of 0.5 mm a D/d of 4.8, a δ/d of 2, and a conical outlet. The average pressure of the two inlet streams was 27 psig. The process solvent was fed to the mixer at a temperature of 54 C by adjusting the temperature from 23 C using a ⅛" coil submersed in a temperature bath. The non-process solvent was fed to the mixer at a temperature of 8 C by adjusting the temperature from 23 C using a ⅛" coil submersed in a separate temperature bath. The mixing velocity was 11.4 m/s.

At steady state, a portion of the effluent from the mixer was collected in a vessel containing 239 g of RO water. The sample were light orange, opalescent, and clear to the eye without any large particles present. A portion was diluted further with RO water to a concentration suitable for analysis by laser photon correlation spectroscopy. The nanoparticles size was 83 nm in diameter. A portion was filtered for sterilization on a 0.22 μm PVDF filter and diluted further for analysis by photon correlation spectroscopy. The nanoparticles size was essentially the same, within 4%, 82 nm in diameter.

We claim:

1. A method for preparing solid nanoparticles by flash precipitation comprising:
   flash precipitating solid nanoparticles comprising at least one amphiphilic copolymer and at least one organic additive target molecule by mixing 1) an organic solvent comprising said at least one amphiphilic copolymer and said at least one organic additive target molecule and 2) water or an aqueous solution comprising a buffering agent or salt,
   wherein said mixing comprises injecting the organic solvent and the water or aqueous solution as liquid streams into a confined mixing chamber,
   wherein said organic solvent is soluble with said water or aqueous solution and
   the mixing of said organic solvent and said water or aqueous solution results in a single product solvent that causes the precipitation of said amphiphilic copolymer and said target molecule as nanoparticles,
   wherein the organic additive target molecule to amphiphilic copolymer ratio by weight is at least 1:4 in said organic solvent,
   wherein the particle size of the resulting nanoparticles is a function of the temperature, the hydrophobic and hydrophilic character of at least one amphiphilic copolymer, and the mixing velocity of the process, and
   wherein the mixing velocity of the organic solvent and the water or aqueous solution is at least 0.1 m/sec.

2. The method of claim 1, wherein at least one amphiphilic copolymer comprises blocks with a minimum contour length equal to the length of at least 5 ethylene units.

3. The method of claim 1, wherein at least one amphiphilic copolymer comprises blocks with a molecular weight of at least 300 g/mole.

4. The method of claim 1, wherein at least one amphiphilic copolymer has a total molecular weight between about 1000 to about 50,000 g/mole.

5. The method of claim 1, wherein at least one amphiphilic copolymer has a total molecular weight of at least 2000 g/mole.

6. The method of claim 1, wherein at least one amphiphilic copolymer exhibits a surface tension when dissolved in water of at least 50 dynes/cm at a concentration of 0.1 weight percent at 25° C.

7. The method of claim 1, wherein the organic solvent is capable of dissolving at least 0.1% of at least one amphiphilic copolymer by weight.

8. The method of claim 1, wherein the organic solvent comprises an ether or an alcohol.

9. The method of claim 8, wherein the organic solvent comprises tetrahydrofuran.

10. The method of claim 1, wherein the concentration of at least one amphiphilic copolymer in the organic solvent is at least 0.1 wt %.

11. The method of claim 10, wherein the concentration of at least one amphiphilic copolymer in the organic solvent is between about 0.3 wt % to about 10.0 wt %.

12. The method of claim 1, wherein the concentration of at least one amphiphilic copolymer in the organic solvent is at least 0.05 wt %.

13. The method of claim 1, wherein the temperature of the organic solvent and the water or aqueous solution is maintained between about 20° C. to about 50° C.

14. The method of claim 13, wherein the temperature of the organic solvent and the water or aqueous solution is maintained at 35° C.

15. The method of claim 1, wherein the pressure during mixing is controlled.

16. The method of claim 1, wherein the pressure during mixing is maintained above 8 psig.

17. The method of claim 1, wherein said at least one organic additive target molecule is continuously added to a mixer with said water or an aqueous solution comprising a buffering agent or salt such that said nanoparticles are continuously produced.

18. The method of claim 1, wherein the organic solvent, the aqueous solution, or both is a liquefied gas.

19. The method of claim 1, wherein at least 85% of the resulting nanoparticles are less than 1060 nm in diameter.

20. The method of claim 19, wherein the average diameter of the resulting nanoparticles is less than about 400 nm.

21. The method of claim 1, further comprising the step of removing the product solvent from the product solvent containing the nanoparticles.

22. The method of claim 21, wherein the product solvent is removed by a process selected from the group consisting of filtration, distillation, evaporation, expansion, lyophilization, and extraction.

23. The method of claim 1, wherein the organic additive target molecule to amphiphilic copolymer ratio by weight is 1:4 to about 20:1.

24. The method of claim 1, wherein at least one organic additive target molecule make up at least 0.2% by weight of the mixture based on initial charges to the mixer.

25. The method of claim 1, wherein at least one organic additive target molecule is selected from the group consisting of pharmaceutical organic actives, pharmaceutical organic precursor compounds, proteins, cyclosporins, immunoactive agents, analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, blood products and substitutes, cardiac inotropic agents, contrast media, corticosteroids, cough suppressants, diagnostic agents, diagnostic imaging agents, diuretics, dopaminergics, haemostatics, immuriological agents, lipid regulating agents, muscle relaxants, parasympathomimetics, parathyroid calcitonin and biphosphonates, prostaglandins, radio-pharmaceuticals, sex hormones, anti-allergic agents, stimulants and anoretics, sympathomimetics, thyroid agents, vasodilators, xanthines, anti-oxidants, preservatives, vitamins, nutrients, antioxidant, agricultural organic compounds, biocides, pesticides, herbicides, fungicides, insecticides, cosmetic products, dyes, reagents, salts, biological markers, magnetic particle precursors, radiopaque materials, β-carotene, a crystalline phase drug, and an amorphous phase drug.

26. The method of claim 25, wherein at least one organic additive target molecule is a vitamin.

27. The method of claim 1, further comprising adding at least one supplemental additive to the organic solvent before mixing or to the organic solvent after mixing.

28. The method of claim 27, wherein at least one supplemental additive is selected from the group consisting of surfactants, gelatin, phospholipid, Pluronics, inert diluents, solubilizing agents, emulsifiers, suspending agents, adjuvants, wetting agents, colloidal dispersants, cellulose, dicalcium phosphate, dodecyl trimethyl ammonium bromide, glycerol, glycerol monostearate, glucose, p-isononylphenoxypolt-(glycidol), glucamides, lecithin (phosphatides), maltosides, magnesium stearate, magnesium aluminum silicate, oils, starch, polyethylene glycols, polyoxyethylene alkyl ethers, polyoxyethylene sorbitan fatty acid esters, poloxamers, polaxamines, silicic acid, sodium citrate, sodium dodecyl sulfate, sodium lauryl sulfate, steric acid, sucrose, tapioca starch, talc, thioglucosides, tragacanth, triethanolamine, Triton X-200®, salt, functional surface modifier, protein, sugar, fatty acid, organic pharmaceutical excipient, inorganic pharmaceutical excipient, pharmaceutically acceptable carrier, and low molecular weight oligomer.

29. The method of claim 25, wherein at least one supplemental additive is tocopherol.

30. The method of claim 27, wherein at least one supplemental additive is added at a concentration by weight of up to a ratio of 2:1 of supplemental additive to organic additive target molecule.

31. The method of claim 1, wherein said flash precipitation is performed in a centripetal mixer, a continuous flash mixer, or a batch flash mixer.

32. The method of claim 1, wherein the mixing of the organic solvent with the water or aqueous solution comprises injecting the organic solvent and the water or aqueous solution into a confined mixing chamber at the same time.

33. The method of claim 32, wherein the organic solvent and the water or aqueous solution are injected into the chamber at about 0.02 m/s to 12.0 m/s.

34. The method of claim 33, wherein said mixing chamber comprises an outlet for continuous flow from said mixing chamber.

35. The method of claim 32, wherein the organic solvent and the water or aqueous solution are injected at each other within said mixing chamber.

36. The method of claim 32, wherein the organic solvent and the water or aqueous solution are injected via separate inlet tubes.

37. The method of claim 36, wherein the distance between the inlet tubes within the mixing chamber is less than 40 times the diameter of the inlet tubes.

38. The method of claim 1, wherein the additive target molecule to amphiphilic copolymer ratio by weight is at least 1:2.

39. The method of claim 1, wherein the additive target molecule to amphiphilic copolymer ratio by weight is at least 1:1.

40. The method of claim 1, wherein the additive target molecule to amphiphilic copolymer ratio by weight is 1:4 to 10:1.

41. The method of claim 1, wherein at least one amphiphilic copolymer comprises a block, graft or random copolymer.

42. The method of claim 1, wherein at least one hydrophobic block of at least one amphiphilic copolymer comprises a subunit selected from the group consisting of acrylate, n-butyl acrylate, t-butyl acrylate, n-butyl methacrylates, isobutyl methacrylate, ethyl methacrylate, isobutyl acrylate, isopropyl acrylate, ethyl acrylate, 2-ethyl acrylate, propyl acrylate, styrene, acrylonitrile, methacrylonitrile, vinyl, vinyl amine, vinyl acetate, vinylversatate, vinylpropionate, vinylformamide, vinylacetamide, vinylpyridines, vinylimidazole, aminoalkyl, aminoalkylacrylate, aminoalkylsmethacrylate, aminoalkyl(meth)acrylamides, and lactides.

43. The method of claim 1, wherein at least one hydrophilic block of at least one amphiphilic copolymer comprises a subunit selected from the group consisting of polyethylene oxide, carboxylic acid, acrylic acid, methacrylic acid, itaconic acid, maleic acid, unsaturated ethylenic monocarboxylic acids, glucosamine, N-acetylglucosamine, and unsaturated ethylenic dicarboxylic acids.

44. The method of claim 1 wherein at least one amphiphilic copolymer is selected from the group consisting of polystyrenes, polyethyleneglycols, polyglutamic acids, hyaluronic acids, polyvinylpyrrolidones, polylysines, polyarginines, alginic acids, polylactides, polyethyleneimines, polyionenes, polyacrylic acids, and polyiminocarboxylates.

45. The method of claim 1, wherein at least one sub-unit forming the hydrophobic blocks of at least one amphiphilic copolymer is selected from the group consisting of acrylates, methacrylates, vinyls, aminoalkyls, styrenes, and lactides.

46. The method of claim 1, wherein at least one sub-unit forming the hydrophilic blocks of at least one amphiphilic copolymer is selected from the group consisting of carboxylic, polyoxyethylenes, unsaturated ethylenic monocarboxylic acids, and unsaturated ethylenic dicarboxylic acids.

47. The method of claim 1, wherein said water or aqueous solution is water.

48. The method of claim 1, wherein said aqueous solution consists of water and a buffering agent or salt.

* * * * *